(12) United States Patent
Bavari et al.

(10) Patent No.: US 8,691,859 B2
(45) Date of Patent: Apr. 8, 2014

(54) BROAD SPECTRUM ANTIBACTERIAL COMPOUNDS

(75) Inventors: Sina Bavari, Frederick, MD (US); Rekha G. Panchal, Frederick, MD (US); Rick Gussio, Frederick, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 1367 days.

(21) Appl. No.: 11/464,001

(22) Filed: Aug. 11, 2006

(65) Prior Publication Data

US 2007/0112048 A1  May 17, 2007

Related U.S. Application Data

(60) Provisional application No. 60/707,531, filed on Aug. 12, 2005, provisional application No. 60/723,442, filed on Oct. 5, 2005.

(51) Int. Cl.

| | | |
|---|---|---|
| *A01N 43/52* | (2006.01) | |
| *A61K 31/415* | (2006.01) | |
| *A01N 43/76* | (2006.01) | |
| *A61K 31/42* | (2006.01) | |
| *A01N 43/78* | (2006.01) | |
| *A61K 31/425* | (2006.01) | |
| *A01N 43/38* | (2006.01) | |
| *A61K 31/405* | (2006.01) | |

(52) U.S. Cl.
USPC ............ 514/394; 514/375; 514/367; 514/415

(58) Field of Classification Search
USPC .................................. 514/394, 375, 367, 415
See application file for complete search history.

(56) References Cited

U.S. PATENT DOCUMENTS

| | | | |
|---|---|---|---|
| 5,965,582 A | 10/1999 | Lebaut et al. | |
| 2005/0148522 A1* | 7/2005 | Baasov et al. | 514/36 |
| 2005/0153945 A1 | 7/2005 | Bavari et al. | |
| 2005/0251345 A1* | 11/2005 | Bavari et al. | 702/19 |

FOREIGN PATENT DOCUMENTS

| | | |
|---|---|---|
| WO | 02/056858 A1 | 7/2002 |
| WO | WO 2004026264 A2 * | 4/2004 |
| WO | 2004/041209 A2 | 5/2004 |
| WO | 2005/033065 A1 | 4/2005 |

OTHER PUBLICATIONS

Anne et al. "Antifungal and Antibacterial Activities of Diarylamidine Derivatives" Antimicrobial agents and chemotherapy, Aug. 1980, pp. 231-239.*

Sheridan, R.P. "The Most Common Chemical Replacements in Drug-Like Compounds" J. Chem. Inf. Comput. Sci, 2002, vol. 42, pp. 103-108.*
Chikvaidze, I."Synthesis of 2,5'-bi-1H-indole derivatives and study of their biocidal properties" Soobshcheniya Akademii Nauk Gruzii, 1995, vol. 152, pp. 307-310.*
Anne, J. et al. (1980) "Antifungal and Antibacterial Activities of Diarylamidine Derivatives" Antimicrobial Agents & Chemotherapy 18(2):231-239.
De. Clercq et al. (1980) "Diaryl Amidine Derivatives as Oncornaviral DNA Polymerase Inhibitors" J. Med. Chem. 23:787-795.
Tidwell et al. (1978) "Diarylamidine Derivatives with One or Both of the Aryl Moieties Consisting of an Indole or Indole-like Ring, Inhibitors of Arginine-Specific Esteroproteases" J. Med. Chem. 21(7):613-623.
Extended European Search Report received in EP06851682, mailed Jun. 26, 2012.
Kucukbay, H. et al. (1995) "Synthesis and Antimicrobial Activity of Substituted Benzimidazole, Bensothiazole and Imidazole Derivatives" Arzneimittel Forschung. Drug Research 45(12):1331-1334.
Nandi, M.M. et al. (1986) "Studies on Potential Antibacterial & Chelating Agents: Part I—Synthesis, Physiochemical Properties & Antibacterial Screening of Some Benzimidazoles" 25B(2):222-224.
Dykstra, C. et al. (1994) "Selective Inhibition of Topoisomerases from Pneumocystis carinii Compared with That of Topoisomerases from Mammalian Cells" Antimicrobial Agents and Chemotherapy 38(9):1890-1898.
Lombardy, R. (1996) "Synthesis and DNA Interactions of Benzimidazole Dication Which Have Activity Against Opportunistic Infections" J. Med Chem 39(7): 1452-1462.
Montecucco, C. et al. (2004) "Stop the Killer: How 1-14 to Inhibit the Anthrax Lethal Factor Metalloprotease" Trends in Biochemical Sciences 29(6):282-285.
Panchal, R. et al. (2004) "Identification of 1-14 Small Molecule Inhibitors of Anthraz Lethal Factor" Nature Structural & Molecular Biology 11(1):67-72.
Hisano, T. et al. (1982) "Synthesis of Benzoaxazoles and Evaluation of their Antifungal, Insecticidal and Herbicidal Activities" Chemical & Pharmaceutical Bulletin 30(8)2996-3004.
Taffs, K. et al. (1961) "Preparation and Oxidation of Some Bisbenzimidazoles and Benzimidazolylhydroxypropionic Acids" Chemical Abstracts, Accession No. 55-16520i.
Steinmann, U. et al. (1986) "Hemodynamic Effects of a Series of New Trypanocidal Idoleamidino Compounds" Drug Development Research 7(2):153-163.
Vinsova, J. et al. (2005) "Highly Lipophilic Benzoxazoles with Potential Antibacterial Activity" Molecules 10:783-793.
International Search Report and the Written Opinion of the International Searching Authority, or the Declaration mailed Sep. 25, 2008 received in PCT/US06/31550.

* cited by examiner

*Primary Examiner* — Kendra D Carter
(74) *Attorney, Agent, or Firm* — Elizabeth Arwine

(57) ABSTRACT

Disclosed herein are methods of inhibiting, reducing or preventing growth of or destroying bacteria of at least one bacterial strain which comprises contacting the bacteria with the compounds disclosed herein. Also disclosed are methods of treating, inhibiting or preventing an infection or intoxication caused by bacteria of at least one bacterial strain in a subject and pharmaceutical and cosmetic compositions comprising the compounds disclosed herein.

18 Claims, 5 Drawing Sheets

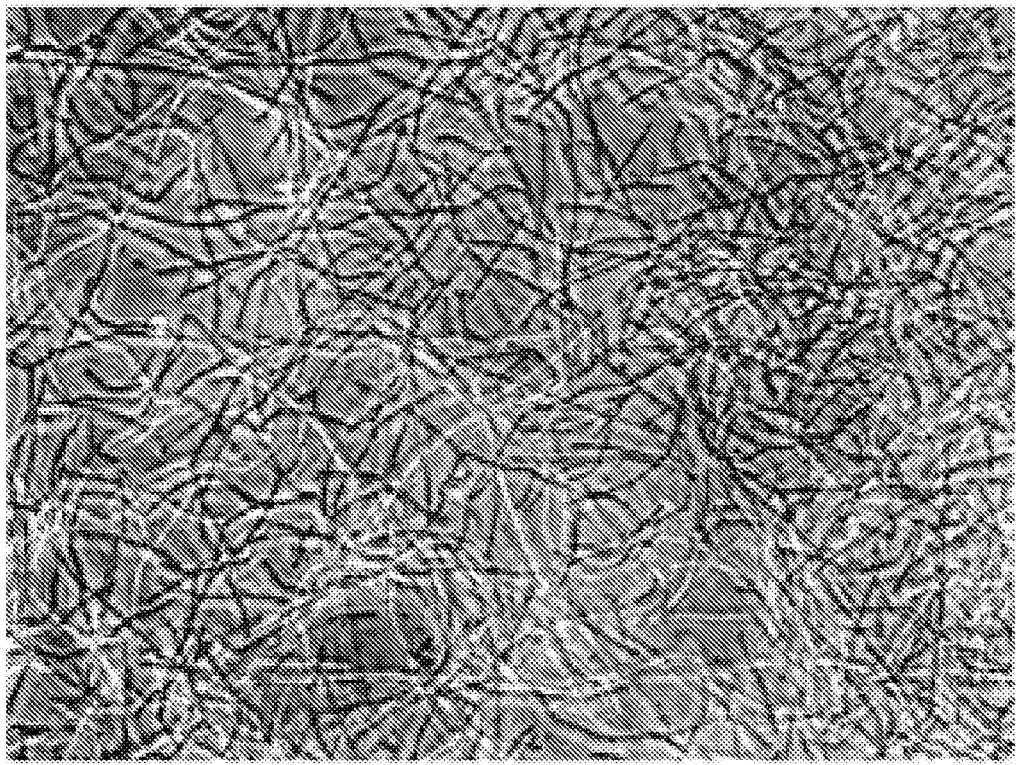
Figure 1A1
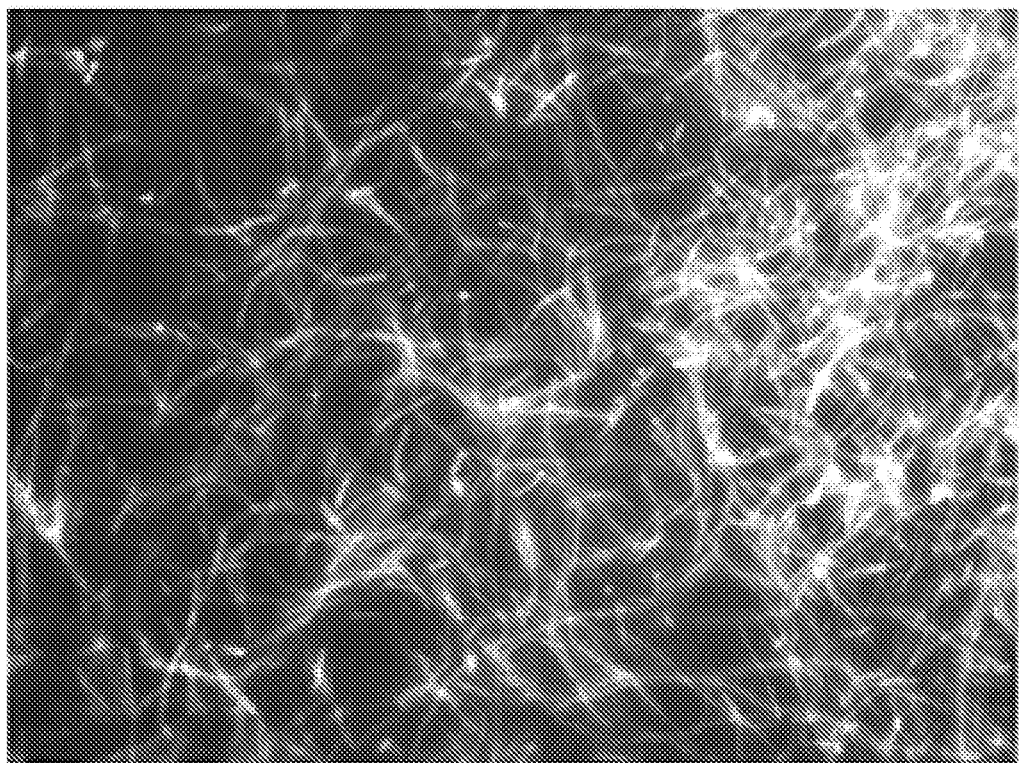
Figure 1A2

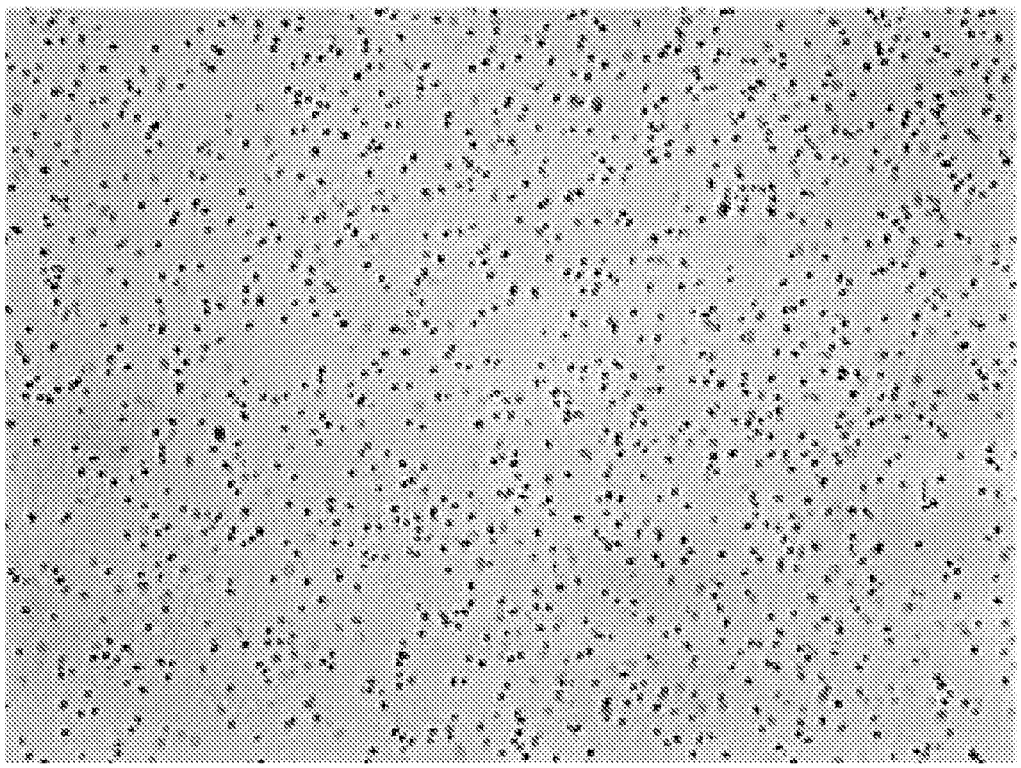
Figure 1B1
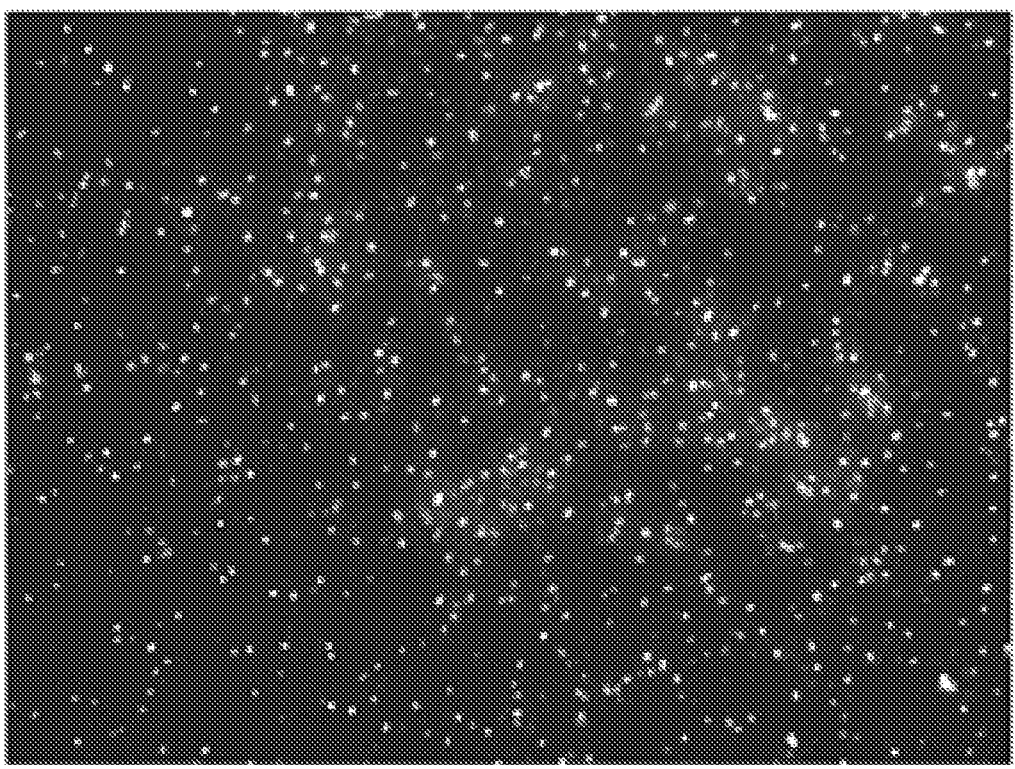
Figure 1B2

| NSC | Structure |
|---|---|
| NSC 317880 | 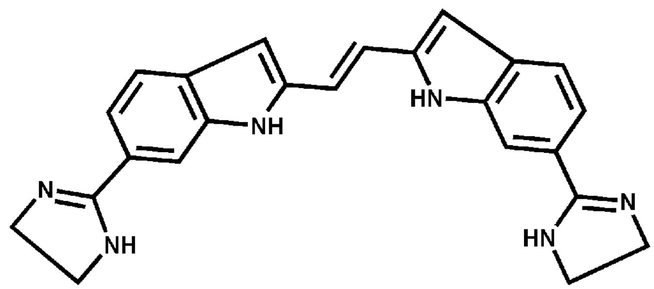 |
| NSC 317881 | 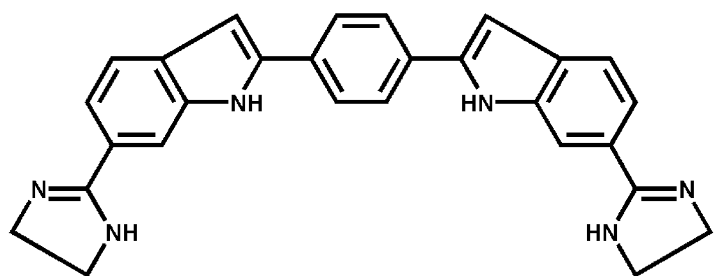 |
| NSC 369718 | 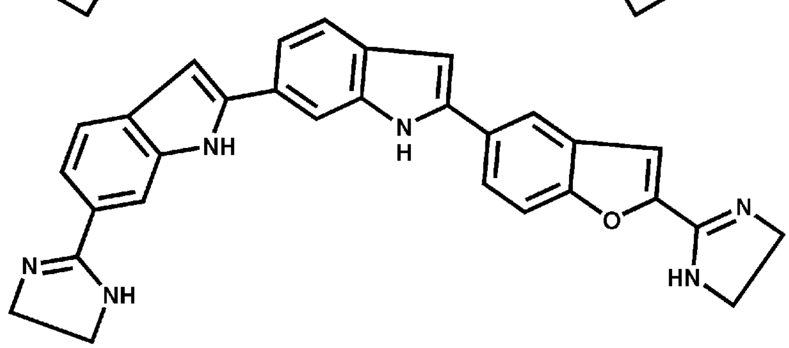 |
| NSC 330687 | 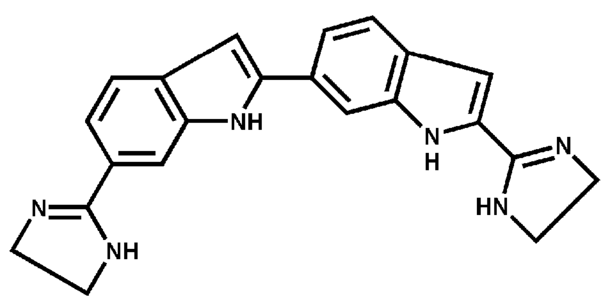 |

BROAD SPECTRUM ANTIBACTERIAL COMPOUNDS

CROSS-REFERENCE TO RELATED APPLICATIONS

This application claims the benefit of U.S. Provisional Patent Application Ser. Nos. 60/707,531, filed 12 Aug. 2005, and 60/723,442, filed 5 Oct. 2005, both of which are herein incorporated by reference in their entirety.

ACKNOWLEDGEMENT OF GOVERNMENT SUPPORT

This invention was made by employees of the United States Army Medical Research and Materiel Command, which is an agency of the United States Government. The Government has certain rights in this invention.

BACKGROUND OF THE INVENTION

1. Field of the Invention

The present invention relates to compounds which exhibit antibacterial properties.

2. Description of the Related Art

Acquired or engineered bacterial resistance to existing antibiotics represents one of the most significant obstacles to protecting both military personnel and civilians from harmful infections. The human induced evolution of bacterial strains resistant to amoxicillin, trimethoprim-sulfamethoxazole, penicillin, and methicillin has been well documented by the medical community, and it is increasingly evident that such microorganisms pose a major threat to public health. However, the most alarming threat to date is the emergence of bacteria that are resistant to vancomycin, the antibiotic that is the last line of defense in the clinic. Furthermore, it is clear that resistance is more likely when newly introduced antibiotics are chemically similar to those that are already ineffective. For example, the emergence of penicillin G resistance was followed by resistance to a structurally similar compound, amoxicillin.

Thus, new antimicrobial compounds possessing novel scaffolds and unique mechanisms of action, are urgently needed.

SUMMARY OF THE INVENTION

The present invention relates to compounds which exhibit antibacterial properties.

Specifically, the compounds of the present invention have the following structural formula:

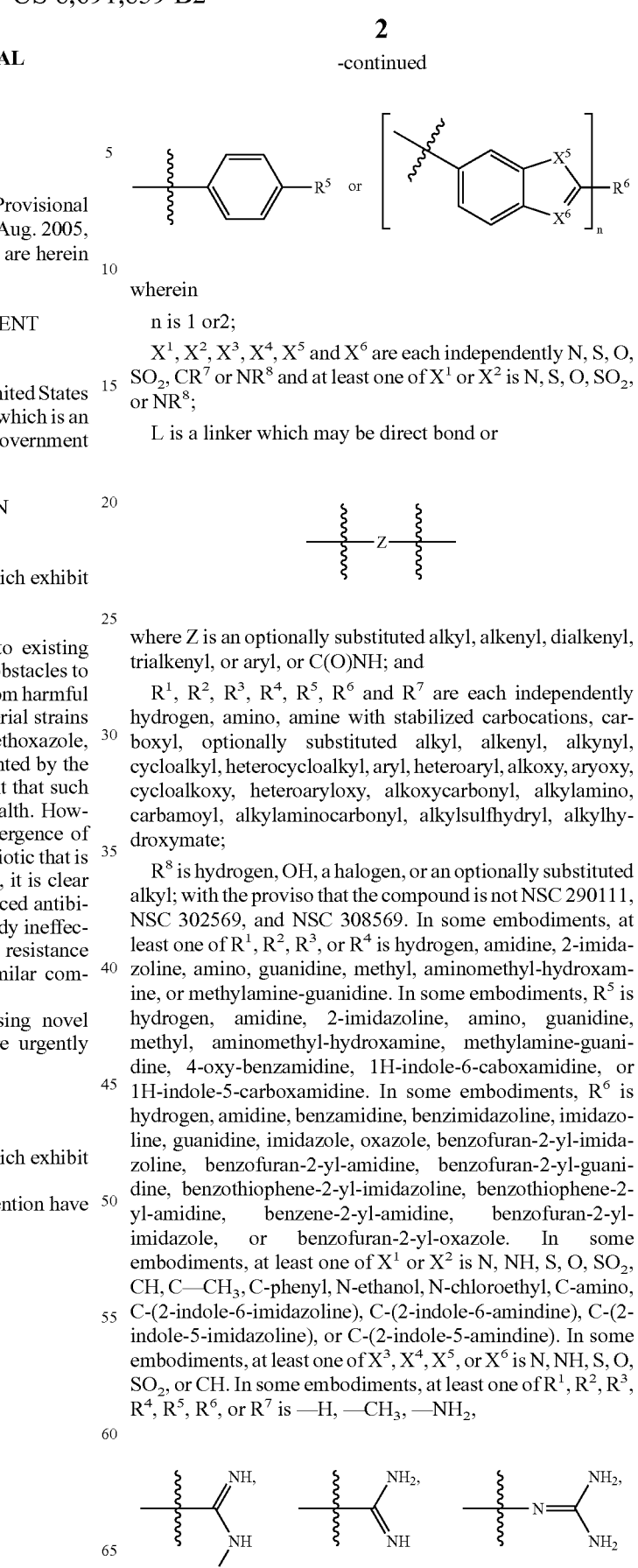

wherein Y is

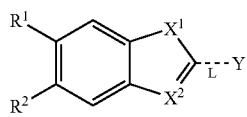

or

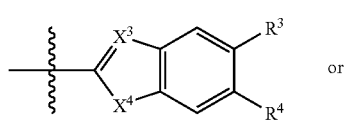

wherein n is 1 or 2;

$X^1$, $X^2$, $X^3$, $X^4$, $X^5$ and $X^6$ are each independently N, S, O, $SO_2$, $CR^7$ or $NR^8$ and at least one of $X^1$ or $X^2$ is N, S, O, $SO_2$, or $NR^8$;

L is a linker which may be direct bond or where Z is an optionally substituted alkyl, alkenyl, dialkenyl, trialkenyl, or aryl, or C(O)NH; and $R^1$, $R^2$, $R^3$, $R^4$, $R^5$, $R^6$ and $R^7$ are each independently hydrogen, amino, amine with stabilized carbocations, carboxyl, optionally substituted alkyl, alkenyl, alkynyl, cycloalkyl, heterocycloalkyl, aryl, heteroaryl, alkoxy, aryoxy, cycloalkoxy, heteroaryloxy, alkoxycarbonyl, alkylamino, carbamoyl, alkylaminocarbonyl, alkylsulfhydryl, alkylhydroxymate;

$R^8$ is hydrogen, OH, a halogen, or an optionally substituted alkyl; with the proviso that the compound is not NSC 290111, NSC 302569, and NSC 308569. In some embodiments, at least one of $R^1$, $R^2$, $R^3$, or $R^4$ is hydrogen, amidine, 2-imidazoline, amino, guanidine, methyl, aminomethyl-hydroxamine, or methylamine-guanidine. In some embodiments, $R^5$ is hydrogen, amidine, 2-imidazoline, amino, guanidine, methyl, aminomethyl-hydroxamine, methylamine-guanidine, 4-oxy-benzamidine, 1H-indole-6-caboxamidine, or 1H-indole-5-carboxamidine. In some embodiments, $R^6$ is hydrogen, amidine, benzamidine, benzimidazoline, imidazoline, guanidine, imidazole, oxazole, benzofuran-2-yl-imidazoline, benzofuran-2-yl-amidine, benzofuran-2-yl-guanidine, benzothiophene-2-yl-imidazoline, benzothiophene-2-yl-amidine, benzene-2-yl-amidine, benzofuran-2-yl-imidazole, or benzofuran-2-yl-oxazole. In some embodiments, at least one of $X^1$ or $X^2$ is N, NH, S, O, $SO_2$, CH, C—$CH_3$, C-phenyl, N-ethanol, N-chloroethyl, C-amino, C-(2-indole-6-imidazoline), C-(2-indole-6-amindine), C-(2-indole-5-imidazoline), or C-(2-indole-5-amindine). In some embodiments, at least one of $X^3$, $X^4$, $X^5$, or $X^6$ is N, NH, S, O, $SO_2$, or CH. In some embodiments, at least one of $R^1$, $R^2$, $R^3$, $R^4$, $R^5$, $R^6$, or $R^7$ is —H, —$CH_3$, —$NH_2$,

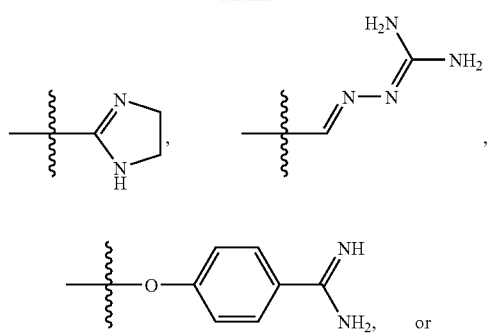

In some embodiments, $R^5$ is —$NH_2$,

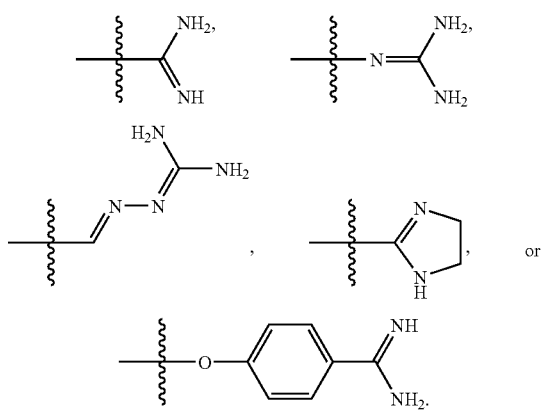

In some embodiments, $R^6$ is

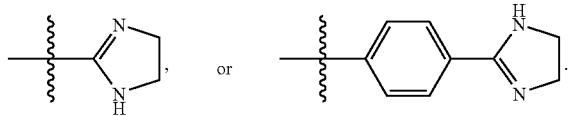

In some embodiments, $R^7$ is —H, —$CH_3$, —$NH_2$,

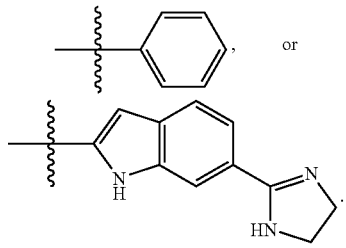

In some embodiments, $R^8$ is —H, —$(CH_2)_2OH$, or —$(CH_2)_2Cl$. In some embodiments, L is a direct bond,

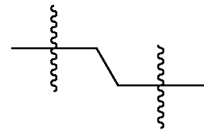

In some embodiments, the compound has the following structural formulae:

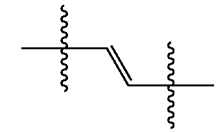

In some embodiments, the compound is NSC 92833, NSC 103699, NSC 103701, NSC 130681, NSC 240890, NSC 240891, NSC 240893, NSC 240894, NSC 240895, NSC 240896, NSC 240897, NSC 240898, NSC 240899, NSC 240900, NSC 266472, NSC 266474, NSC 266475, NSC 266476, NSC 266477, NSC 266482, NSC 278995, NSC 278996, NSC 278997, NSC 278999, NSC 290107, NSC 290108, NSC 290109, NSC 291103, NSC 294199, NSC 294200, NSC 294201, NSC 294202, NSC 294203, NSC 294204, NSC 294206, NSC 294207, NSC 294208, NSC 294494, NSC 300509, NSC 300510, NSC 300511, NSC 300512, NSC 308570, NSC 308571, NSC 308572, NSC 308573, NSC 308574, NSC 317880, NSC 317881, NSC 317883, NSC 317884, NSC 317885, NSC 317886, NSC 317887, NSC 330687, NSC 330688, NSC 330689, NSC 330690, NSC 341082, NSC 341907, NSC 341909, NSC 341910, NSC 341911, NSC 352341, NSC 369718, NSC 369721, NSC 607617, or NSC 12155. In some embodiments, the compound is NSC 317880, NSC 317881, NSC 330687, or NSC 369718.

In some embodiments, the present invention provides a method of inhibiting, reducing or preventing growth of or destroying bacteria of at least one bacterial strain which comprises contacting the bacteria with an effective amount of at least one compound provided herein. In some embodiments, the bacterial strain is belongs to *Bacillus, Burkholderia, Enterobacter, Escherichia, Helicobacter, Klebsiella, Mycobacterium, Neisseria, Pseudomonas, Staphylococcus, Streptococcus, Yersinia*, or drug resistant strains thereof. In some embodiments, the bacterial strain is *B. anthracis, B. brevis, B. licheniformis, B. megaterium, B. pumilus, B. subtilis, B. vollum, B. cepacia, B. mallei, M. pseudomallei, B. thailandensis, E. coli, E. feacalis, E. faecium, K. pneumoniae; P. aeruginosa, S. aureous, Y pestis*, or drug resistant strains thereof. In some embodiments, the bacteria are of two or more bacterial strains. In some embodiments, the bacteria are on or in an object, such as clothing, a table top, eating utensils, water, food, air, or anything which may come into contact with or may be consumed by a mammal such as a human.

In some embodiments, the present invention provides a method of treating, inhibiting or preventing an infection or intoxication caused by bacteria of at least one bacterial strain in a subject which comprises administering to the subject a therapeutically effective amount of at least one compound provided herein. In some embodiments, the bacterial strain is belongs to *Bacillus, Burkholderia, Enterobacter, Escherichia, Helicobacter, Klebsiella, Mycobacterium, Neisseria, Pseudomonas, Staphylococcus, Streptococcus, Yersinia*, or drug resistant strains thereof. In some embodiments, the bacterial strain is *B. anthracis, B. brevis, B. licheniformis, B. megaterium, B. pumilus, B. subtilis, B. vollum, B. cepacia, B. mallei, M. pseudomallei, B. thailandensis, E. coli, E. feacalis, E. faecium, K pneumoniae; P. aeruginosa, S. aureous, Y. pestis*, or drug resistant strains thereof. In some embodiments, the bacteria are of two or more bacterial strains. In some embodiments, the compound is in the form of a pharmaceutical or cosmetic composition. In some embodiments, a supplementary active compound is administered to the subject. The supplementary active compound may be formulated with a compound of the present invention or provided as a separate composition.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein.

FIG. 1A2 shows a GFP fluorescence image of GFP-sterne spores that were treated with a DMSO control and the growth of vegetative cells after 22 hours.

FIG. 1B1 shows a phase contrast image of GFP steme spores treated with NSC 317881 (MIC of 0.084 μg/ml) for 22 hours.

FIG. 1B2 shows a GFP fluorescent image of GFP sterne spores treated with NSC 317881 (MIC of 0.084 μg/ml) for 22 hours.

FIG. 1C is a graph showing time dependent inhibition of GFP fluorescence by a few compounds of the present invention at their MIC concentrations.

FIG. 1D is a graph showing growth inhibition of GFP sterne vegetative cells at different concentrations of a few compounds of the present invention.

FIG. 2 is a graph which shows that NSC 317881 does not have any observable effect on steme spore germination.

FIG. 3 is a graph which shows that NSC 317881 kills GFP steme spores in a time dependent manner.

FIG. 4 shows the structural formulas of NSC 317880, NSC 317881, NSC 330687, and NSC 369718.

DETAILED DESCRIPTION OF THE INVENTION

The present invention is directed to the antibacterial properties of bi- and triarylimidazolidines and bi- and triarylamidines. The compounds of the present invention do not structurally resemble any of the current classes of clinically used antibiotics, including penicillins, cephalosporins, monobactams, carbapenems, fluoroquinolones, macrolides, aminoglycosides, streptogramins, oxazolidinones, metronidazole, clindamycin, and vancomycin. The compounds of the present invention are active against a broad range of gram positive and gram negative bacteria, including drug resistant strains such as vancomycin resistant enterococcus, methicillin resistant *Staphylococcus aureus* (MRSA) and ciproflaxcin resistant *B. anthracis*. As provided herein, some of the compounds of the present invention exhibit MIC values ranging from about 0.021 to about 22 μg/ml. Some of the compounds exemplified herein inhibit the outgrowth of *B. anthracis* spores and kill *B. anthracis* vegetative spores in the early stages of germination.

The compounds of the present invention have the following Structural Formula I:

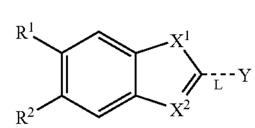

where Y is 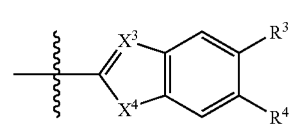 or

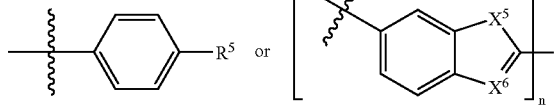

Figure 1C:
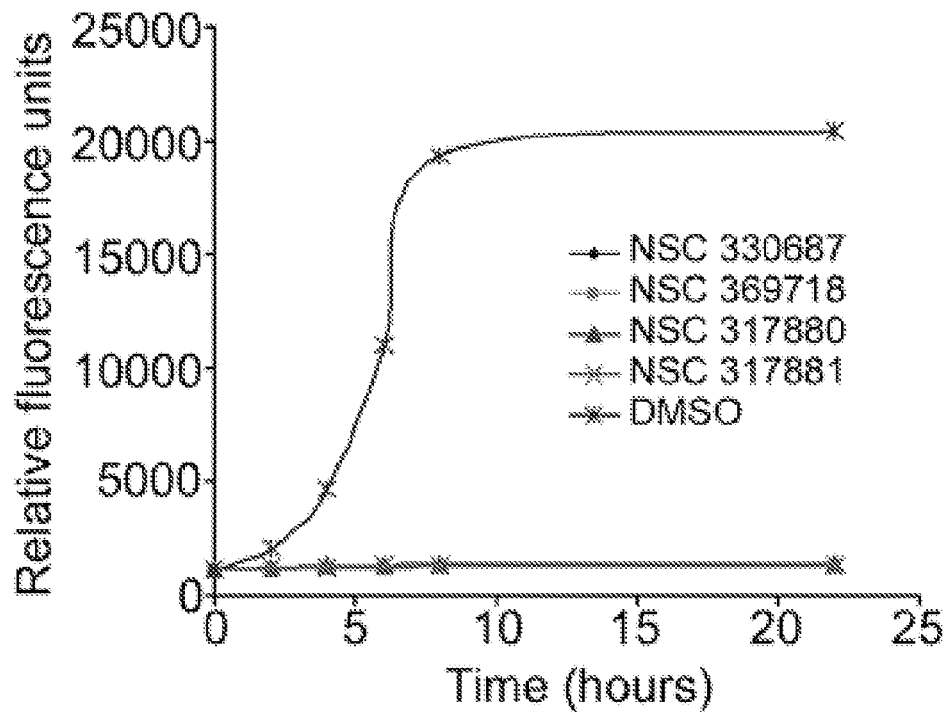
FIG. 1A1 shows a phase contrast image of GFP-steme spores that were treated with a DMSO control and the growth of vegetative cells after 22 hours.

wherein
n is 1 or 2;
$X^1$, $X^2$, $X^3$, $X^4$, $X^5$ and $X^6$ are each independently N, S, O, $SO_2$, $CR^7$ or $NR^8$ and at least one of $X^1$ or $X^2$ is N, S, O, $SO_2$, or $NR^8$;

L is a linker which may be a direct bond or

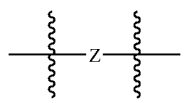

where Z is an optionally substituted alkyl, alkenyl, dialkenyl, trialkenyl, or aryl, or C(O)NH; and $R^1$, $R^2$, $R^3$, $R^4$, $R^5$, $R^6$ and $R^7$ are each independently hydrogen, amino, amine with stabilized carbocations, carboxyl, optionally substituted alkyl, alkenyl, alkynyl, cycloalkyl, heterocycloalkyl, aryl, heteroaryl, alkoxy, aryoxy, cycloalkoxy, heteroaryloxy, alkoxycarbonyl, alkylamino, carbamoyl, alkylaminocarbonyl, alkylsulfhydryl, alkylhydroxymate;

$R^8$ is hydrogen, OH, a halogen, or an optionally substituted alkyl; with the proviso that the compound is not NSC 290111, NSC 302569, and NSC 308569.

It is noted that in the structural formulas of the present invention, the bond orders of the specified rings may vary when the various heteroatoms introduce specific requirements to satisfy aromaticity, prevent antiaromaticity, and stabilize tautomeric forms due to localization. Thus, the appropriate bond orders of the ring structures in the structural formulas of the present invention are contemplated herein.

In some embodiments, $R^1$ is hydrogen, amidine, 2-imidazoline, amino, guanidine, methyl, aminomethyl-hydroxamine, or methylamine-guanidine.

In some embodiments, $R^2$ is hydrogen, amidine, 2-imidazoline, amino, guanidine, methyl, aminomethyl-hydroxamine, or methylamine-guanidine.

In some embodiments, $R^3$ is hydrogen, amidine, 2-imidazoline, amino, guanidine, methyl, aminomethyl-hydroxamine, or methylamine-guanidine.

In some embodiments, $R^4$ is hydrogen, amidine, 2-imidazoline, amino, guanidine, methyl, aminomethyl-hydroxamine, or methylamine-guanidine.

In some embodiments, $R^5$ is hydrogen, amidine, 2-imidazoline, amino, guanidine, methyl, aminomethyl-hydroxamine, methylamine-guanidine, 4-oxy-benzamidine, 1H-indole-6-caboxamidine, or 1H-indole-5-carboxamidine.

In some embodiments, $R^6$ is hydrogen, amidine, benzamidine, benzimidazoline, imidazoline, guanidine, imidazole, oxazole, benzofuran-2-yl-imidazoline, benzofuran-2-yl-amidine, benzofuran-2-yl-guanidine, benzothiophene-2-yl-imidazoline, benzothiophene-2-yl-amidine, benzene-2-yl-amidine, benzofuran-2-yl-imidazole, or benzofuran-2-yl-oxazole.

In some embodiments, $X^1$ is N, NH, S, O, $SO_2$, CH, C—$CH_3$, C-phenyl, N-ethanol, N-chloroethyl, C-amino, C-(2-indole-6-imidazoline), C-(2-indole-6-amidine), C-(2-indole-5-imidazoline), or C-(2-indole-5-amidine).

In some embodiments, $X^2$ is N, NH, S, O, $SO_2$, CH, C—$CH_3$, C-phenyl, N-ethanol, N-chloroethyl, C-amino, C-(2-indole-6-imidazoline), C-(2-indole-6-amidine), C-(2-indole-5-imidazoline), or C-(2-indole-5-amidine).

In some embodiments, $X^3$ is N, NH, S, O, $SO_2$, or CH.

In some embodiments, $X^4$ is N, NH, S, O, $SO_2$, or CH.

In some embodiments, $X^5$ is N, NH, S, O, $SO_2$, or CH.

In some embodiments, $X^6$ is N, NH, S, O, $SO_2$, or CH.

In some embodiments, at least one of $R^1$, $R^2$, $R^3$, $R^4$, $R^5$, $R^6$ or $R^7$ is —H, —$CH_3$,

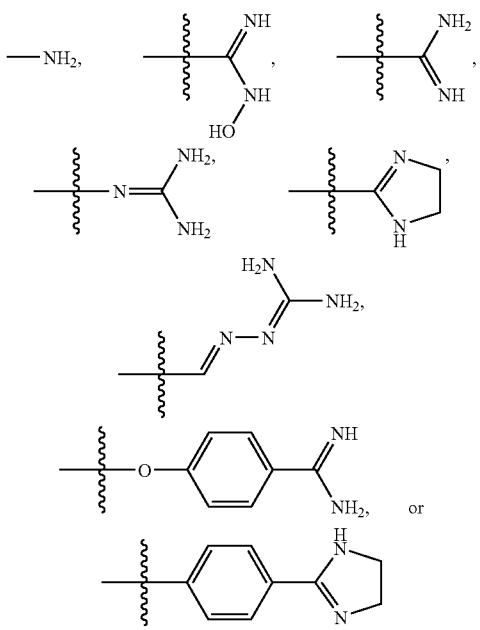

In some embodiments, $R^5$ is —$NH_2$,

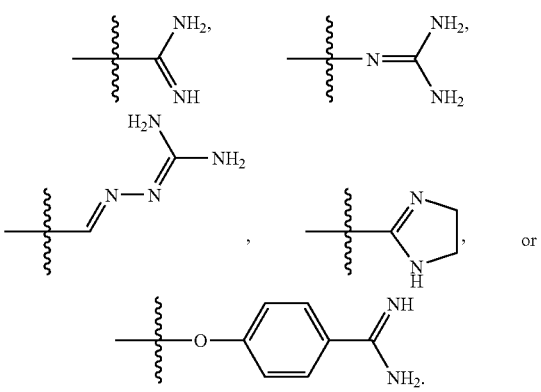

In some embodiments, $R^6$ is

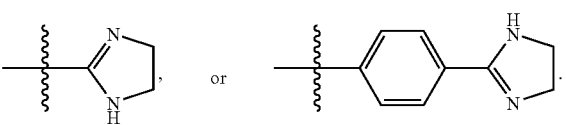 [SMILES: *C1=NCCN1 ; "or" ; *c1ccc(C2=NCCN2)cc1]

In some embodiments $R^7$ is —H, —CH$_3$, —NH$_2$,

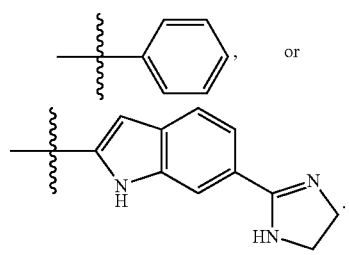

or

In some embodiments, $R^8$ is —H, —(CH$_2$)$_2$OH, or —(CH$_2$)$_2$OH, or —(CH$_2$)$_2$Cl.

In some embodiments, L is a direct bond,

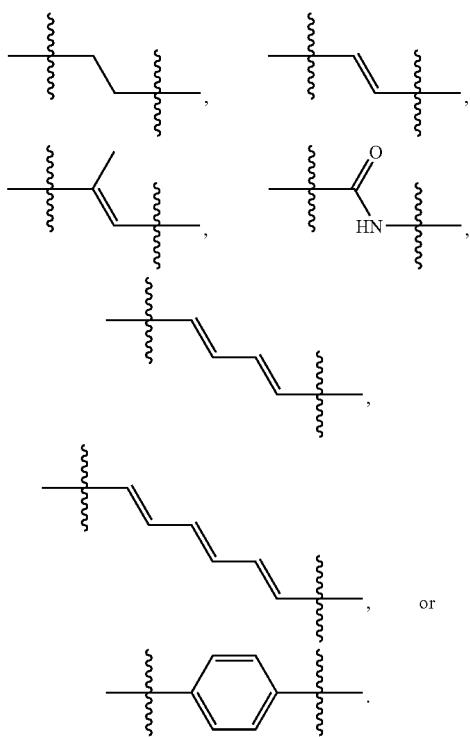

In some embodiments, compounds of the present invention have the following structural formulae:

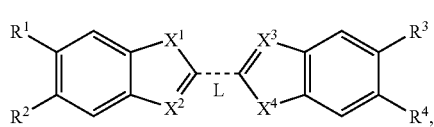
(A)

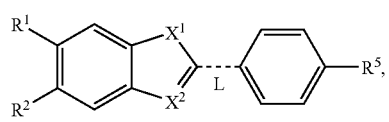
(B)

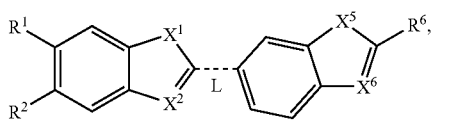
(C)

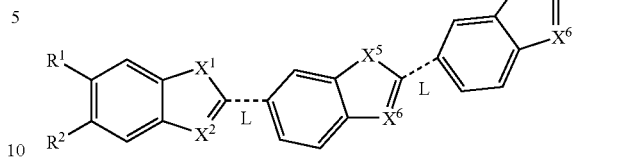
(D)

wherein
n is 1 or 2;
$X^1, X^2, X^3, X^4, X^5$ and $X^6$ are each independently N, S, O, SO$_2$, CR$^7$ or NR$^8$ and at least one of $X^1$ or $X^2$ is N, S, O, SO$_2$, or NR$^8$;
L is a linker which may be a direct bond or

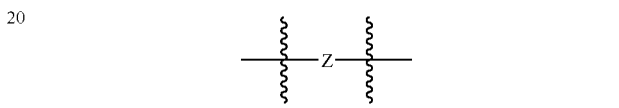

where Z is an optionally substituted alkyl, alkenyl, dialkenyl, trialkenyl, or aryl, or C(O)NH; and
$R^1$, $R^2$, $R^3$, $R^4$, $R^5$, $R^6$ and $R^7$ are each independently hydrogen, amino, amine with stabilized carbocations, carboxyl, optionally substituted alkyl, alkenyl, alkynyl, cycloalkyl, heterocycloalkyl, aryl, heteroaryl, alkoxy, aryoxy, cycloalkoxy, heteroaryloxy, alkoxycarbonyl, alkylamino, carbamoyl, alkylaminocarbonyl, alkylsulfhydryl, alkylhydroxymate;
$R^8$ is hydrogen, OH, a halogen, or an optionally substituted alkyl; with the proviso that the compound is not NSC 290111, NSC 302569, and NSC 308569.

In accordance with a convention used in the art,

is used in structural formulas herein to depict the bond that is the point of attachment of the moiety or substituent to the core or backbone structure.

Where chiral carbons are included in chemical structures, unless a particular orientation is depicted, both sterioisomeric forms are intended to be encompassed.

A "halo" or "halogen" means fluorine, bromine, chlorine, and iodine.

An "alkyl" is intended to mean a straight or branched chain monovalent radical of saturated and/or unsaturated carbon atoms and hydrogen atoms, such as methyl (Me), ethyl (Et), propyl (Pr), isopropyl (i-Pr), butyl (n-Bu), isobutyl (i-Bu), t-butyl (t-Bu), (sec-Bu), and the like, which may be unsubstituted (i. e., contain only carbon and hydrogen) or substituted by one or more suitable substituents as defined below. A "lower alkyl group" is intended to mean an alkyl group having from 1 to 8 carbon atoms in its chain.

A "haloalkyl" refers to an alkyl that is substituted with one or more same or different halo atoms, e.g., —CH$_2$Cl, —CF$_3$, —CH$_2$CF$_3$, —CH$_2$CCl$_3$, and the like.

An "alkenyl" means straight and branched hydrocarbon radicals having from 2 to 8 carbon atoms and at least one double bond such as ethenyl, 3-buten-1-yl, 2-ethenylbutyl, 3-hexen-1-yl, and the like. The term "alkenyl" includes, cycloalkenyl, and heteroalkenyl in which 1 to 3 heteroatoms selected from O, S, N or substituted nitrogen may replace carbon atoms.

An "alkynyl" means straight and branched hydrocarbon radicals having from 2 to 8 carbon atoms and at least one triple bond and includes, but is not limited to, ethynyl, 3-butyn-1-yl, propynyl, 2-butyn-1-yl, 3-pentyn-1-yl, and the like.

A "cycloalkyl" is intended to mean a non-aromatic monovalent monocyclic or polycyclic radical having from 3 to 14 carbon atoms, each of which may be saturated or unsaturated, and may be unsubstituted or substituted by one or more suitable substituents as defined herein, and to which may be fused one or more aryl groups, heteroaryl groups, cycloalkyl groups, or heterocycloalkyl groups which themselves may be unsubstituted or substituted by one or more substituents. Examples of cycloalkyl groups include cyclopropyl, cycloheptyl, cyclooctyl, cyclodecyl, cyclobutyl, adamantyl, norpinanyl, decalinyl, norbornyl, cyclohexyl, and cyclopentyl.

A "heterocycloalkyl" is intended to mean a non-aromatic monovalent monocyclic or polycyclic radical having 1-5 heteroatoms selected from nitrogen, oxygen, and sulfur, and may be unsubstituted or substituted by one or more suitable substituents as defined herein, and to which may be fused one or more aryl groups, heteroaryl groups, cycloalkyl groups, or heterocycloalkyl groups which themselves may be unsubstituted or substituted by one or more substituents. Examples of heterocycloalkyl groups include oxiranyl, pyrrolidinyl, piperidyl, tetrahydropyran, and morpholinyl.

An "aryl" (Ar) is intended to mean an aromatic monovalent monocyclic or polycyclic radical comprising generally between 5 and 18 carbon ring members, which may be unsubstituted or substituted by one or more suitable substituents as defined herein, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Examples include phenyl, biphenyl, 1,2,3,4-tetrahydronaphthyl, naphthyl, anthryl, and phenanthryl.

A "heteroaryl" is intended to mean an aromatic monovalent monocyclic or polycyclic radical comprising generally between 4 and 18 ring members, including 5-heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Examples include thienyl, furanyl, thiazolyl, triazolyl, imidazolyl, isoxazolyl, oxadiazolyl, tetrazolyl, pyridyl, pyrrolyl, thiadiazolyl, oxadiazolyl, oxathiadiazolyl, thiatriazolyl, pyrimidinyl, isoquinolinyl, quinolinyl, napthyridinyl, phthalimidyl, benzimidazolyl, and benzoxazolyl.

A "hydroxy" is intended to mean the radical —OH.

An "alkoxy" is intended to mean the radical —OR, where R is an alkyl group. Exemplary alkoxy groups include methoxy, ethoxy, propoxy, and the like.

A "hydroxyalkyl" means an alkyl that is substituted with one, two, or three hydroxy groups, e.g. hydroxymethyl, 1 or 2-hydroxyethyl, 1,2-, 1,3-, or 2,3-dihydroxypropyl, and the like.

A "haloalkoxy" refers to an —O—(haloalkyl) group. Examples include trifluoromethoxy, tribromomethoxy, and the like.

A "cycloalkoxy" is intended to mean the radical —OR, where R is acycloalkyl or heterocycloalkyl group.

An "aryloxy" is intended to mean the radical —OR, where R is an aryl or heteroaryl group. Examples include phenoxy, pyridinyloxy, furanyloxy, thienyloxy, pyrimidinyloxy, pyrazinyloxy, and the like.

An "acyl" is intended to mean a —C(O)—R radical, where R is an alkyl or aryl, bonded through a carbonyl group. Acyl groups include acetyl, benzoyl, and the like.

An "aralkyl" means an alkyl that is substituted with an aryl group. Examples include —CH$_2$-phenyl, —(CH$_2$)$_2$-phenyl, —(CH$_2$)$_3$-phenyl, —CH$_3$CH(CH$_3$)CH$_2$-phenyl, and the like.

A "heteroaralkyl" group means an alkyl that is substituted with a heteroaryl group. Examples include —CH$_2$-pyridinyl, —(CH$_2$)$_2$-pyrimidinyl, —(CH$_2$)$_3$-imidazolyl, and the like.

A "carboxy" is intended to mean the radical —C(O)OH.

An "alkoxycarbonyl" is intended to mean the radical —C(O)OR, where R is an alkyl group. Examples include methoxycarbonyl, ethoxycarbonyl, and the like.

An "amino" is intended to mean the radical —NH$_2$.

An "amine with stabilized carbocations" are comprised of two or more NH$_2$ groups that contribute lone pairs to configure a highly stabilized carbocation. Examples include amidines and guanidines.

An "alkylamino" is intended to mean the radical —NHR, where R is an alkyl group or the radical —NR$^a$R$^b$, where R$^a$ and R$^b$ are each independently an alkyl group. Examples of alkylamino groups include methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino, N-n-hexyl-N-methylamino and the like.

An "alkylsulfhydryl" is intended to mean R-SH, where R is an alkyl group. Examples include methylsulfhydryl, ethylsulfhydryl, n-propylsulfhydryl, iso-propylsulfhydryl, n-butylsulfhydryl, iso-butylsulfhydryl, secondary-butylsulfhydryl, tertiary-butylsulfhydryl. Preferable alkylsulfhydryl groups are methylsulfhydryl, ethylsulfhydryl, n-propylsulfhydryl, n-butylsulfhydryl, and the like.

An "alkylhydroxymate" is intended to mean the radical R—C(O)NH—OH, where R is an alkyl group. Examples include methylhydroxymate, ethylhydroxymate, n-propylhydroxymate, iso-propylhydroxymate, n-butylhydroxymate, iso-butylhydroxymate, secondary-butylhydroxymate, tertiary-butylhydroxymate. Preferable alkylhydroxymate groups are methylhydroxymate, ethylhydroxymate, n-propylhydroxymate, n-butylhydroxymate, and the like. A "carbamoyl" is intended to mean the radical —C(O)NH$_2$.

An "alkylaminocarbonyl" is intended to mean the radical —C(O)NHR, where R is an alkyl group or the radical —C(O)NR$^a$R$^b$, where R$^a$ and R$^b$ are each independently an alkyl group. Examples include methylaminocarbonyl, ethylaminocarbonyl, dimethylaminocarbonyl, methylethylaminocarbonyl, and the like.

A "mercapto" is intended to mean the radical —SH.

An "alkylthio" is intended to mean the radical —SR, where R is an alkyl or cycloalkyl group. Examples of alkylthio groups include methylthio, ethylthio, n-propylthio, isopropylthio, tert-butylthio, n-pentylthio, n-hexylthio, cyclopropylthio, cyclobutylthio, cyclopentylthio, cyclohexylthio, and the like.

An "arylthio" is intended to mean the radical —SR, where R is an aryl or heteroaryl group. Examples include phenylthio, pyridinylthio, furanylthio, thienylthio, pyrimidinylthio, and the like.

A "thioacyl" is intended to mean a —C(S)—R radical, where R is an alkyl or aryl, bonded through a thiol group.

An "alkylsulfonyl" is intended to mean the radical —$SO_2$R, where R is an alkyl group. Examples include methylsulfonyl, ethylsulfonyl, n-propylsulfonyl, iso-propylsulfonyl, n-butylsulfonyl, iso-butylsulfonyl, secondary-butylsulfonyl, tertiary-butylsulfonyl. Preferable alkylsulfonyl groups are methylsulfonyl, ethylsulfonyl, n-propylsulfonyl, n-butylsulfonyl, and the like.

A "leaving group" (Lv) is intended to mean any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wuts, Protective Groups in Organic Synthesis, $3^{rd}$ edition, John Wiley and Sons, New York, N.Y. (1999).

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxyl groups, carboxyl groups, amino groups, alkylamino groups, dialkylamino groups, carbamoyl groups, arylthio groups, heteroarylthio groups, and the like.

In general, the various moieties or functional groups for variables in the formulae may be "optionally substituted" by one or more suitable "substituents". The term "substituent" or "suitable substituent" is intended to mean any suitable substituent that may be recognized or selected, such as through routine testing, by those skilled in the art. Illustrative examples of useful substituents are those found in the exemplary compounds that follow, as well as a halogen; $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (═O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$-O. All of these substituents may optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

It is understood that while a compound of the general structural formulas herein may exhibit the phenomenon of tautomerism, the structural formulas within this specification expressly depict only one of the possible tautomeric forms. It is therefore to be understood that the structural formulas herein are intended to represent any tautomeric form of the depicted compound and is not to be limited merely to a specific compound form depicted by the structural formulas.

It is also understood that the structural formulas are intended to represent any configurational form of the depicted compound and is not to be limited merely to a specific compound form depicted by the structural formulas.

Some of the compounds of the present invention may exist as single stereoisomers (i.e., essentially free of other stereoisomers), racemates, or mixtures of enantiomers, diastereomers, or both when they contain one or more stereogenic centers as designated by R or S according to the Cahn-Ingold-Prelog rules whether the absolute or relative configuration is known. All such single stereoisomers, racemates and mixtures thereof are intended to be within the scope of the present invention.

Some of the compounds in the present invention may exist as geometric isomers as the result of containing a stereogenic double bond. In such cases, they may exist either as pure or mixtures of cis or trans geometric isomers or (E) and (Z) designated forms according to the Cahn-Ingold-Prelog rules and include compounds that adopt a double bond configuration as a result of electronic delocalization.

As generally understood by those skilled in the art, an optically pure compound having one or more chiral centers (i.e., one asymmetric atom producing unique tetrahedral configuration) is one that consists essentially of one of the two possible enantiomers (i.e., is enantiomerically pure), and an optically pure compound having more than one chiral center is one that is both diastereomerically pure and enantiomerically pure. If the compounds of the present invention are made synthetically, they may be used in a form that is at least 90% optically pure, that is, a form that comprises at least 90% of a single isomer (80% enantiomeric excess (e.e.) or diastereomeric excess (d.e.), more preferably at least 95% (90% e.e. or d.e.), even more preferably at least 97.5% (95% e.e. or d.e.), and most preferably at least 99% (98% e.e. or d.e.).

Additionally, the structural formulas herein are intended to cover, where applicable, solvated as well as unsolvated forms of the compounds. A "solvate" is intended to mean a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulas include compounds having the indicated structure, including the hydrated as well as the non-hydrated forms.

As indicated above, the compounds of the invention also include active tautomeric and stereoisomeric forms of the compounds of the present invention, which may be readily obtained using techniques known in the art. For example, optically active (R) and (S) isomers may be prepared via a stereospecific synthesis, e.g., using chiral synthons and chiral reagents, or racemic mixtures may be resolved using conventional techniques.

Additionally, the compounds of the invention include pharmaceutically acceptable salts, multimeric forms, prodrugs, active metabolites, precursors and salts of such metabolites of the compounds of the present invention.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

The term "multimer" refers to multivalent or multimeric forms of active forms of the compounds of the invention. Such "multimers" may be made by linking or placing multiple copies of an active compound in close proximity to each other, e.g., using a scaffolding provided by a carrier moiety. Multimers of various dimensions (i.e., bearing varying numbers of copies of an active compound) may be tested to arrive at a multimer of optimum size with respect to binding site interactions. Provision of such multivalent forms of active binding compounds with optimal spacing between the binding site moieties may enhance binding site interactions. See e.g. Lee et al., (1984) Biochem. 23:4255. The artisan may control the multivalency and spacing by selection of a suitable carrier moiety or linker units. Useful moieties include molecular supports comprising a multiplicity of functional groups that can be reacted with functional groups associated with the active compounds of the invention. A variety of carrier moieties may be used to build highly active multimers, including proteins such as BSA (bovine serum albumin), peptides such as pentapeptides, decapeptides, pentadecapeptides, and the like, as well as non-biological compounds selected for their beneficial effects on absorbability, transport, and persistence within the target organism. Functional groups on the carrier moiety, such as amino, sulfhydryl, hydroxyl, and alkylamino groups, may be selected to obtain stable linkages to the compounds of the invention, optimal spacing between the immobilized compounds, and optimal biological properties.

"A pharmaceutically acceptable prodrug" is a compound that may be converted under physiological conditions or by solvolysis to the specified compound or to a pharmaceutically acceptable salt of such compound, or a compound that is biologically active with respect to the intended pharmacodynamic effect. "A pharmaceutically active metabolite" is intended to mean a pharmacologically active product produced through metabolism in the body of a specified compound or salt thereof. Prodrugs and active metabolites of a compound may be identified using routine techniques known in the art. See, e.g., Bertolini, G. et al., (1997) J. Med. Chem. 40:2011-2016; Shan, D. et al., *J. Pharm. Sci.,* 86(7):765-767; Bagshawe K., (1995) Drug Dev. Res. 34:220-230; Bodor, N., (1984) Advances in Drug Res. 13:224-331; Bundgaard, H., *Design of Prodrugs* (Elsevier Press, 1985); and Larsen, I. K., *Design and Application of Prodrugs,* Drug Design and Development (Krogsgaard-Larsen et al., eds., Harwood Academic Publishers, 1991).

If the compound of the present invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the present invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from basic amino acids, such as lysine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of compounds that are solids, it is understood by those skilled in the art that the compound of the present invention and salts may exist in different crystal or polymorphic forms, all of which are intended to be within the scope of the present invention and specified structural formulas.

The compounds of the present invention are useful in inhibiting, reducing or preventing growth of or destroying bacteria of at least one bacterial strain. The compounds of the present invention are also treating, inhibiting or preventing an infection or intoxication caused by bacterial of at least one bacterial strain in a subject. The bacteria belong to various gram positive and gram negative bacteria strains including *Bacillus, Burkholderia, Enterobacter, Escherichia, Helicobacter, Klebsiella, Mycobacterium, Neisseria, Pseudomonas, Staphylococcus, Streptococcus, Yersinia* and the like, including drug resistance strains. In preferred embodiments, the bacteria is *B. anthracis* (including Ames strain and ciprofloxacin resistant Ames strain) *B. anth*1024 (K1021), *B. brevis, B. licheniformis, B. megaterium, B. pumilus, B. subtilis, B. vollum*, and spores thereof, *B. cepacia, B. mallei, M. pseudomallei*, and *B. thailandensis; E. coli, E. feacalis, E. faecium*, and vancomycin resistant strains thereof, *K. pneumoniae; P. aeruginosa*, preferably PAO1; *S. aureus* and methicillin resistant *S. aureous; Y. pestis*; or a combination thereof.

The activity of the compounds of the present invention may be measured by any of the methods available to those skilled in the art, including in vitro and in vivo assays. Examples of suitable assays for activity measurements are provided herein. Properties of the compounds of the present invention may be assessed, for example, by using one or more of the assays set out in the Examples below. Other pharmacological methods may also be used to determine the efficacy of the compounds a subject suffering from a given disease or disorder. The compounds of the present invention may be used in combination with or as a substitution for treatments known in the art.

The therapeutically effective amounts of the compounds of the invention for treating the diseases or disorders described above in a subject can be determined in a variety of ways known to those of ordinary skill in the art, e.g. by administering various amounts of a particular compound to a subject afflicted with a particular condition and then determining the effect on the subject. Typically, therapeutically effective amounts of a compound of the present invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect. It will be understood, however, that the specific dose levels for any particular subject will depend upon a variety of factors including the activity of the specific compound employed, the age, body weight, general health, sex, diet, time of administration, route of administration, and rate of excretion, drug combination and the severity of the particular disease.

Frequency of dosage may also vary depending on the compound used and the particular disease treated It will also be appreciated that the effective dosage of the compound used for treatment may increase or decrease over the course of a particular treatment. Changes in dosage may result and become apparent by standard diagnostic assays known in the art. In some instances chronic administration may be required.

The compounds of the present invention may be administered before, during, after, or a combination thereof exposure to bacteria.

As provided herein, an "effective amount" is intended to mean that amount of a compound that is sufficient to reduce, prevent or inhibit bacterial growth as compared with a negative control. A "therapeutically effective amount" of a compound of the present invention, a prodrug, an active metabolite, or a salt thereof, is a quantity sufficient to, when administered to a subject, reduce, prevent or inhibit bacterial growth. Also, as used herein, a "therapeutically effective amount" of a compound of the present invention is an amount which prevents, inhibits, suppresses, or reduces a given clinical condition in a subject as compared to a control. As defined herein, a therapeutically effective amount of a compound of the present invention may be readily determined by one of ordinary skill by routine methods known in the art.

The pharmaceutical formulations of the invention comprise at least one compound of the present invention and may be prepared in a unit-dosage form appropriate for the desired mode of administration. The pharmaceutical formulations of the present invention may be administered for therapy by any suitable route including oral, rectal, nasal, topical (including buccal and sublingual), dermal, mucosal, vaginal and parenteral (including subcutaneous, intramuscular, intravenous and intradermal). It will be appreciated that the preferred route will vary with the condition and age of the recipient, the nature of the condition to be treated, and the chosen compound of the present invention.

The compound can be administered alone, but will generally be administered as pharmaceutical formulations suitable for administration. Pharmaceutical formulations known in the art contemplated herein. Pharmaceutical formulations of this invention comprise a therapeutically effective amount of at least one compound of the present invention, and an inert, pharmaceutically or cosmetically acceptable carrier or diluent. As used herein the language "pharmaceutically acceptable carrier" or a "cosmetically acceptable carrier" is intended to include any and all solvents, dispersion media, coatings, antibacterial and antifungal agents, isotonic and absorption delaying agents, and the like, compatible with pharmaceutical or cosmetic administration. Except insofar as any conventional media or agent is incompatible with the active compound, use thereof in the formulation is contemplated.

Descriptions of suitable pharmaceutically acceptable carriers, formulations, and factors involved in their selection, are found in a variety of readily available sources, e.g., Remington's Pharmaceutical Sciences, $17^{th}$ ed., Mack Publishing Company, Easton, Pa., 1985, which is incorporated herein by reference.

Supplementary active compounds can also be incorporated into the formulations. Supplementary active compounds include antibiotics, antiprotozoal agents, antifungal agents, and antiproliferative agents known in the art, analgesics and other compounds commonly used to treat diseases and disorders associated with bacterial infection and toxic side effects of bacterial infection including intoxication by a toxin.

Antibiotics include penicillin, cloxacillin, dicloxacillin, methicillin, nafcillin, oxacillin, ampicillin, amoxicillin, bacampicillin, azlocillin, carbenicillin, mezlocillin, piperacillin, ticarcillin, azithromycin, clarithromycin, clindamycin, erythromycin, lincomycin, demeclocycline, doxycycline, minocycline, oxytetracycline, tetracycline, quinolone, cinoxacin, nalidixic acid, fluoroquinolone, ciprofloxacin, enoxacin, grepafloxacin, levofloxacin, lomefloxacin, norfloxacin, ofloxacin, sparfloxacin, trovafloxacin, bacitracin, colistin, polymyxin B, sulfonamide, trimethoprim-sulfamethoxazole, co-amoxyclav, cephalothin, cefuroxime, ceftriaxone, vancomycin, gentamicin, amikacin, metronidazole, chloramphenicol, nitrofurantoin, co-trimoxazole, rifampicin, isoniazid, pyrazinamide, kirromycin, thiostrepton, micrococcin, fusidic acid, thiolactomycin, fosmidomycin, and the like.

Antiprotozoal agents include chloroquine, doxycycline, mefloquine, metronidazole, eplornithine, furazolidone, hydroxychloroquine, iodoquinol, pentamidine, mebendazole, piperazine, halofantrine, primaquine, pyrimethamine sulfadoxine, doxycycline, clindamycin, quinine sulfate, quinidine gluconate, quinine dihydrochloride, hydroxychloroquine sulfate, proguanil, quinine, clindamycin, atovaquone, azithromycin, suramin, melarsoprol, eflornithine, nifurtimox, amphotericin B, sodium stibogluconate, pentamidine isethionate, trimethoprim-sulfamethoxazole, pyrimethamine, sulfadiazine, and the like.

Antifungal agents include amphotericin B, fluconazole, itraconazole, ketoconazole, potassium iodide, flucytosine, and the like.

Antiproliferative agents such as altretamine, amifostine, anastrozole, arsenic trioxide, bexarotene, bleomycin, busulfan, capecitabine, carboplatin, carmustine, celecoxib, chlorambucil, cisplatin, cisplatin-epinephrine gel, cladribine, cytarabine liposomal, daunorubicin liposomal, daunorubicin daunomycin, dexrazoxane, docetaxel, doxorubicin, doxorubicin liposomal, epirubicin, estramustine, etoposide phosphate, etoposide VP-16, exemestane, fludarabine, fluorouracil 5-FU, fulvestrant, gemicitabine, gemtuzumabozogamicin, goserelin acetate, hydroxyurea, idarubicin, ifosfamide, imatinib mesylate, irinotecan, letrozole, leucovorin, levamisole, liposomal daunorubicin, melphalan L-PAM, mesna, methotrexate, methoxsalen, mitomycin C, mitoxantrone, paclitaxel, pamidronate, pegademase, pentostain, porfimer sodium, streptozocin, talc, tamoxifen, temozolamide, teniposide VM-26, topotecan, toremifene, tretinoin, ATRA, valrubicin, vinorelbine, zoledronate, steroids, and the like.

Supplementary active compounds also include those which inhibit botulinum neurotoxin serotype A light chain metalloprotease activity, anthrax lethal factor protease activity, and other bacterial toxins and proteases known in the art.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i. e., the concentration of the test compound which achieves a half-maximal inhibition of symptoms) as determined in cell culture. Such information can be used to more accurately determine useful doses in humans. Levels in plasma may be measured, for example, by high performance liquid chromatography.

High Throughput Screening of Small Molecules against GFP-sterne Spores and Vegetative Cells To examine the effect of small molecule compounds on *B. anthracis* spores and vegetative cells, the sterne strain that endogenously expresses green fluorescent protein was used. See Burnett, et al. (2005) Nat Rev. Drug Discov. 4:281-297, which is herein incorporated by reference. The sterne strain contains the pXO 1 plasmid that produces the anthrax toxins but it does not produce the capsule, as it does not contain the pXO2 plasmid. A total of 71 compounds from National Cancer Institute's open repository were screened at concentrations ranging from 40 µM to 0.03 µM against heat activated, ungerminated GFP sterne spores and vegetative cells. GFP fluorescence measurements using methods known in the art were taken at different time intervals. FIG. 1 shows the results of a few compounds that were tested on heat activated, ungerminated GFP sterne spores and vegetative cells.

Figure 1D:
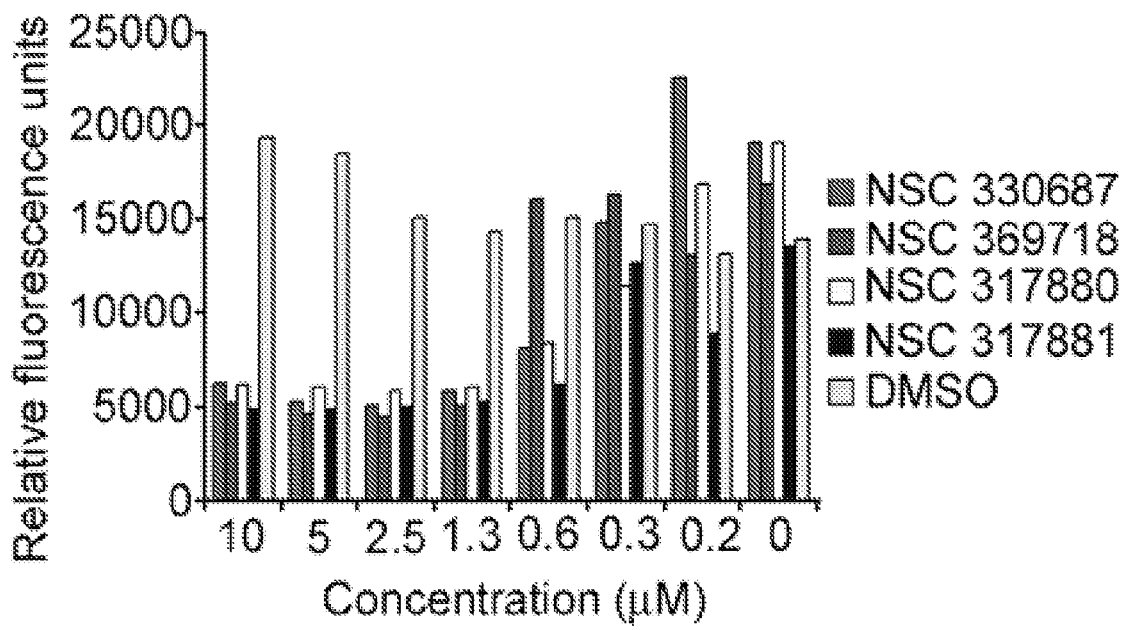
Figure 2:
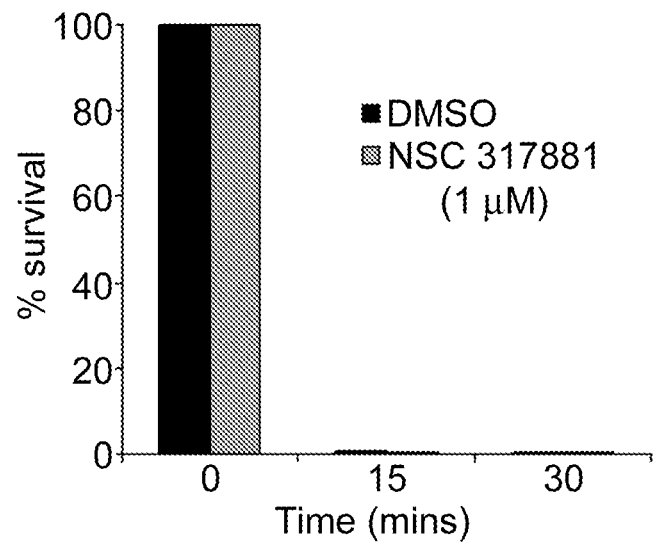

FIG. 1A1 shows GFP sterne spores treated with DMSO (control) germinated and produced long rod shaped bacteria which exhibited GFP fluorescence as provided in FIG. 1A2. By contrast, FIGS. 1B1 and 1B2 show that the compounds of the present invention inhibited the outgrowth of the sterne spores. Specifically, FIG. 1B1 shows a loss in spore refractility and FIG. 1B2 shows increasing phase dark, thereby suggesting that the sterne spores germinated; however, the bacteria failed to outgrow. This outgrowth inhibition was further confirmed by a fluorescence plate reader assay known in the art.

The fluorescence plate reader assay showed no increase in GFP fluorescence as compared to a control as provided in FIG. 1C. The dose dependent effects of a few compounds of the present invention on GFP expressing vegetative cells is shown in FIG. 1D. A list of 71 different compounds screened, along with their minimum inhibitory concentration (MIC) values when tested on *B. anthracis* GFP sterne spores and vegetative cells, is summarized in Table 1.

TABLE 1

| | | MIC (µg/ml) | |
|---|---|---|---|
| | NSC Number | *B. anthracis* spores | *B. anthracis* vegetative cells |
| 2-[2-(5,6-dimethyl-1H-benzoimidazol-2-yl)ethenyl]-5,6-dimethyl-1H-benzoimidazole | 92833 | >12.64 | >12.64 |
| 2-[2-(1H-benzoimidazol-2-yl)ethenyl]-1H-benzoimidazole | 103699 | >10.4 | >10.4 |
| 2-[2-[2-(1H-benzoimidazol-2-yl)ethenyl]benzoimidazol-1-yl]ethanol | 103701 | >12.16 | >12.16 |
| 1-(2-chloroethyl)-2-[2-[1-(2-chloroethyl)benzoimidazol-2-yl]ethenyl]benzoimidazole | 130681 | | |
| 2-(4-carbamimidoylphenyl)benzothiophene-6-carboximidamide; 2-hydroxypropanoic acid | 240890 | >19.00 | >19.00 |
| 2-(4-carbamimidoylphenyl)benzothiophene-5-carboximidamide | 240891 | >14.68 | >14.68 |
| 2-(4-carbamimidoylphenyl)benzofuran-5-carboximidamide | 240893 | >14.04 | >14.04 |
| 2-(4-carbamimidoylphenyl)-3H-benzoimidazole-5-carboximidamide | 240894 | >14.04 | >14.04 |
| 2-(4-carbamimidoylphenyl)indazole-5-carboximidamide | 240895 | >14.04 | >14.04 |
| 2-(4-carbamimidoylphenyl)benzotriazole-5-carboximidamide | 240896 | >14.08 | >14.08 |
| 2-(4-carbamimidoylphenyl)-3-phenyl-1H-indole-6-carboximidamide | 240897 | 8.52 | 17.04 |
| 2-[4-(4-carbamimidoylphenoxy)phenyl]-1H-indole-6-carboximidamide | 240898 | 4.42 | 4.42 |

TABLE 1-continued

|  | NSC Number | MIC (μg/ml) | |
|---|---|---|---|
|  |  | *B. anthracis* spores | *B. anthracis* vegetative cells |
| 2-[(E)-2-(5-carbamimidoylbenzofuran-2-yl)ethenyl]benzofuran-5-carboximidamide | 240899 | >16.68 | >16.68 |
| 4-[3-(4-carbamidoylphenyl)oxazol-5-yl]benzenecarboximidamide | 240900 | >15.12 | >15.12 |
| 2-[(E)-2-(5-carbamimidoylbenzothiophen-2-yl)ethenyl]benzofuran-5-carboximidamide | 266472 | 8.66 | 17.32 |
| 2-[(E)-2-(5-carbamimidoyl-3-methyl-benzofuran-2-yl)ethenyl]-3-methyl-benzofuran-5-carboximidamide | 266474 | >17.80 | >17.80 |
| 2-[(E)-2-(5-carbamimidoyl-3H-benzoimidazol-2-yl)ethenyl]-3H-benzoimidazole-5-carboximidamide | 266475 | >16.68 | >16.68 |
| 2-[(E)-1-(5-carbamimidoylbenzofuran-2-yl)prop-1-en-2-yl]benzofuran-5-carboximidamide | 266476 | >17.24 | >17.24 |
| 2-[2-(5-carbamimidoylbenzofuran-2-yl)ethyl]benzofuran-5-carboximidamide | 266477 | >16.76 | >16.76 |
| 2-(4-aminophenyl)-1,1-dioxo-benzothiophen-6-amine | 266482 | >10.88 | >10.88 |
| 6-(4,5-dihydro-1H-imidazol-2-yl)-2-[4-(4,5-dihydro-1H-imidazol-2-yl)phenyl]-1H-indole | 278995 | >16.08 | >16.08 |
| 2-[2-4-(4,5-dihydro-1H-imidazol-2-yl)phenyl]benzothiophen-6-yl]-4,5-dihydro-1H-imidazole | 278996 | >16.76 | >16.76 |
| 2-[2-4-(4,5-dihydro-1H-imidazol-2-yl)phenyl]benzofuran-5-yl]-4,5-dihydro-1H-imidazole | 278997 | >16.12 | >16.12 |
| 2-[2-[(E)-2-[5-(4,5-dihydro-1H-imidazol-2-yl)benzofuran-2-yl]ethenyl]benzofuran-5-yl]-4,5-dihydro-1H-imidazole | 278999 | >18.76 | >18.76 |
| 2-[(E)-2-(5-carbamimidoylbenzofuran-2-yl)ethenyl]-1H-indole-5-carboximidamide | 290107 | 8.32 | >16.64 |
| 5-(4,5-dihydro-1H-imidazol-2-yl)-2-[(E)-2-[5-(4,5-dihydro-1H-imidazol-2-yl)benzofuran-2-yl]ethenyl]-1H-indole | 290108 | 18.48 | >18.48 |
| 2-[2-(5-carbamimidoylbenzofuran-2-yl)ethyl]-1H-indole-6-carboximidamide | 290109 similar compound 49 | 8.36 | 8.36 |
| 5-(4,5-dihydro-1H-imidazol-2-yl)-N-[4-(4,5-dihydro-1H-imidazol-2-yl)phenyl]benzofuran-2-carboxamide | 290111 compound 71 | 17.84 | >17.84 |
| 2-[(E)-2-(5-carbamimidoylbenzofuran-2-yl)ethenyl]benzofuran-5-carboximidamide; methanesulfonic acid | 291103 | >21.48 | >21.48 |
| 2-[(E)-2-(6-carbamimidoylbenzofuran-2-yl)ethenyl]benzofuran-6-carboximidamide | 294199 | 8.34 | 16.68 |
| 2-[(E)-2-(6-carbamimidoylbenzofuran-2-yl)ethenyl]-1H-indole-6-carboximidamide | 294200 | 2.08 | 4.16 |
| 6-(4,5-dihydro-1H-imidazol-2-yl)-2-[(E)-2-[6-(4,5-dihydro-1H-imidazol-2-yl)benzofuran-2-yl]ethenyl]-1H-indole | 294201 | 4.68 | 18.72 |
| 2-[(E)-2-(5-carbamimidoylbenzofuran-2-yl)ethenyl]benzofuran-6-carboximidamide | 294202 | >16.68 | >16.68 |
| 2-[(E)-2-(6-carbamimidoylbenzofuran-2-yl)ethenyl]-1H-indole-5-carboximidamide | 294203 | 16.64 | >16.64 |
| 5-(4,5-dihydro-1H-imidazol-2-yl)-2-[(E)-2-[6-(4,5-dihydro-1H-imidazol-2-yl)benzofuran-2-yl]ethenyl]-1H-indole | 294204 | 18.72 | >18.72 |
| 6-(4,5-dihydro-1H-imidazol-2-yl)-N-[4-(4,5-dihydro-1H-imidazol-2-yl)phenyl]-1H-indole-2-carboxamide | 294206 | 8.9 | 17.8 |
| 6-carbamimidoyl-N-(4-carbamimidoylphenyl)benzofuran-2-carboxamide | 294207 | >15.76 | >15.76 |
| 6-(4,5-dihydro-1H-imidazol-2-yl)-N-[4-(4,5-dihydro-1H-imidazol-2-yl)phenyl]benzofuran-2-carboxamide | 294208 | >17.84 | >17.84 |
| 2-[2-[(E)-2-[6-(4,5-dihydro-1H-imidazol-2-yl)benzofuran-2-yl]ethenyl]benzofuran-6-yl]-4,5-dihydro-1H-imidazole | 294494 | 18.76 | 18.76 |
| 3-amino-2-(4-carbamimidoylphenyl)-1H-indole-6-carboximidamide | 300509 | >14.6 | >14.6 |
| 4-[5-(4-carbamimidoylphenyl)thiophen-2-yl]benzenecarboximidamide | 300510 | 15.72 | >15.72 |
| 2-[(1E,3E)-4-(5-carbamimidoylbenzofuran-2-yl)buta-1,3-dienyl]benzofuran-5-carboximidamide | 300511 | 2.215 | 17.72 |
| 2-[(E)-2-(4-carbamimidoylphenyl)ethenyl]benzofuran-5-carboximidamide | 300512 | >15.08 | >15.08 |
| No name | 302569 | >22.76 | >22.76 |
| 2-[2-4-(4,5-dihydro-1H-imidazol-2-yl)phenyl]benzothiophen-5-yl]-4,5-dihydro-1H-imidazole | 308569 | >16.76 | >16.76 |
| 2-[2-[(E)-2-[4-(4,5-dihydro-1H-imidazol-2-yl)phenyl]ethenyl]benzofuran-5-yl]-4,5-dihydro-1H-imidazole | 308570 | 17.16 | 17.16 |
| 2-[2-[(1E,3E)-4-[5-(4,5-dihydro-1H-imidazol-2-yl)benzofuran-2-yl]buta-1,3-dienyl]benzofuran-5-yl]-4,5-dihydro-1H-imidazole | 308571 | 9.9 | 19.8 |
| 2-[(1E,3E)-4-(4-carbamimidoylphenyl)buta-1,3-dienyl]benzofuran-5-carboximidamide | 308572 | 8.06 | 16.12 |
| 2-[2-[(1E,3E)-4-[4-(4,5-dihydro-1H-imidazol-2-yl)phenyl]buta-1,3-dienyl]benzofuran-5-yl]-4,5-dihydro-1H-imidazole | 308573 | 18.2 | 18.2 |
| 2-[(1E,3E,5E)-6-(5-carbamimidoylbenzofuran-2-yl)hexa-1,3,5-trienyl]benzofuran-5-carboximidamide | 308574 | 2.345 | 9.38 |

TABLE 1-continued

| | NSC Number | MIC (μg/ml) B. anthracis spores | B. anthracis vegetative cells |
|---|---|---|---|
| 6-(4,5-dihydro-1H-imidazol-2-yl)-2-[(E)-2-[6-(4,5-dihydro-1H-imidazol-2-yl)-1H-indol-2-yl]ethenyl]-1H-indole | 317880 | 0.292 | 1.168 |
| 6-(4,5-dihydro-1H-imidazol-2-yl)-2-[4-[6-(4,5-dihydro-1H-imidazol-2-yl)-1H-indol-2-yl]phenyl]-1H-indole | 317881 | 0.162 | 0.646 |
| 2-[2-[(E)-2-[4-(4,5-dihydro-1H-imidazol-2-yl)phenyl]ethenyl]benzothiophen-5-yl]-4,5-dihydro-1H-imidazole | 317883 | 17.80 | 17.80 |
| 2-[(E)-2-(4-carbamimidoylphenyl)ethenyl]-1H-indole-5-carboximidamide | 317884 | 15.04 | >15.04 |
| 5-(4,5-dihydro-1H-imidazol-2-yl)-2-[(E)-2-[4-(4,5-dihydro-1H-imidazol-2-yl)phenyl]ethenyl]-1H-indole | 317885 | >17.12 | >17.12 |
| 2-[(E)-2-(4-carbamimidoylphenyl)ethenyl]-1H-indole-6-carboximidamide | 317886 | 7.52 | 15.02 |
| 6-(4,5-dihydro-1H-imidazol-2-yl)-2-[(E)-2-[4-(4,5-dihydro-1H-imidazol-2-yl)phenyl]ethenyl]-1H-indole | 317887 | 8.56 | >17.12 |
| 2-(4,5-dihydro-1H-imidazol-2-yl)-6-[6-(4,5-dihydro-1H-imidazol-2-yl)-1H-indol-2-yl]-1H-indole | 330687 | 0.551 | 1.102 |
| 6-(4,5-dihydro-1H-imidazol-2-yl)-2-[6-(4,5-dihydro-1H-imidazol-2-yl)-1H-indol-2-yl]-1H-indole | 330688 | 0.551 | 1.102 |
| 2-(diaminomethylidene)indole-6-carboximidamide | 330689 | >10.96 | >10.96 |
| 6-(4,5-dihydro-1H-imidazol-2-yl)-2-[(E)-2-[4-[4-(4,5-dihydro-1H-imidazol-2-yl)phenoxy]phenyl]ethenyl]-1H-indole | 330690 | 2.6 | 2.6 |
| Glycine, N-acetyl-, compound with 2,2'-(1,{2-ethenediyl)bis[5-benzofurancarboximidamide]} (2:1) | 341082 | >23.16 | >23.16 |
| 6-(4,5-dihydro-1H-imidazol-2-yl)-2-[(E)-2-[2-(4,5-dihydro-1H-imidazol-2-yl)-1H-indol-6-yl]ethenyl]-1H-indole | 341907 | 9.34 | 18.68 |
| 2-[[2-[4-[(E)-(diaminomethylenehydrazinylidene)methyl]phenyl]benzothiophen-6-yl]methylideneamino]guanidine | 341909 | 4.51 | 18.04 |
| 2-[2-[4-(diaminomethylideneamino)phenyl]benzothiophen-5-yl]guanidine | 341910 | 15.88 | >15.88 |
| 6-(4,5-dihydro-1H-imidazol-2-yl)-3-[6-(4,5-dihydro-1H-imidazol-2-yl)-1H-indol-2-yl]-2-[4-(4,5-dihydro-1H-imidazol-2-yl)phenyl]-1H-indole | 341911 | 24.88 | 24.88 |
| 6-(4,5-dihydro-1H-imidazol-2-yl)-3-[6-(4,5-dihydro-1H-imidazol-2-yl)-1H-indol-2-yl]-2-[4-(4,5-dihydro-1H-imidazol-2-yl)phenyl]-1H-indole | 352341 | 6.82 | 13.64 |
| 6-(4,5-dihydro-1H-imidazol-2-yl)-2-[2-[2-(4,5-dihydro-1H-imidazol-2-yl)benzofuran-5-yl]-1H-indol-6-yl]-1H-indole | 369718 | 0.348 | 0.696 |
| 5-(4,5-dihydro-1H-imidazol-2-yl)-2-[2-[4-(4,5-dihydro-1H-imidazol-2-yl)phenyl]-3H-benzoimidazol-5-yl]-3H-benzoimidazole | 369721 | 1.39 | 22.28 |
| 2-[(Z)-2-(5-carbamimidoylbenzofuran-2-yl)ethenyl]benzofuran-5-carboximidamide | 607617 | >13.76 | >13.76 |
| 1,3-bis(4-amino-2-methyl-quinolin-6-yl)urea | 12155 | 4.45 | 17.8 |

*The structural formulas of these compounds are known in the art and may be obtained from various sources including the World Wide Web at dtp.nci.nih.gov/dtpstandard/ChemData/index.jsp and ncbi.nlm.nih.gov/entrez/query.fcgi?CMD=&DB=PubMed and are herein incorporated by reference.

Screening of the Most Potent Antibacterial Compounds against both Gram Positive and Gram Negative Bacteria To determine if the compounds were capable of acting against a broad spectrum of gram positive and gram negative bacteria, the four most potent from the screen against GFP sterne spores (NSC 317880, NSC 317881, NSC 330687, and NSC 369718) were tested at varying concentrations on 20 different bacterial strains. Visual inspections of the plates, as well as absorbance readings at $OD_{600}$, were taken to determine the MICs of the compounds. The MIC values of these four compounds against the different bacterial strains are provided in Table 2.

TABLE 2

MIC values of 4 compounds against selected gram positive and gram negative bacteria

| Strain | NSC 317880 (μg/ml) | NSC 317881 (μg/ml) | NSC 330687 (μg/ml) | NSC 369718 (μg/ml) |
|---|---|---|---|---|
| Gram positive bacteria | | | | |
| *B. anthracis* Ames | 0.584 | 0.32 | 1.103 | 1.392 |
| Cipro resistant Ames | 0.584 | 1.292 | 1.103 | 0.348 |
| *B. anth*1024 | 1.168 | 0.162 | 0.551 | 0.348 |
| **B. brevis* | 0.584 | 0.646 | 0.276 | 0.174 |
| **B. licheniformis* | 2.335 | 0.646 | 2.206 | 1.392 |
| **B. megaterium* | 0.584 | 0.323 | 0.551 | 0.348 |

TABLE 2-continued MIC values of 4 compounds against selected
gram positive and gram negative bacteria

| Strain | NSC 317880 (µg/ml) | NSC 317881 (µg/ml) | NSC 330687 (µg/ml) | NSC 369718 (µg/ml) |
|---|---|---|---|---|
| *B. pumilus | 0.146 | 0.021 | 0.138 | 0.348 |
| *B. vollum | 0.584 | 0.324 | 0.551 | 0.348 |
| Ames spores | 0.146 | 0.162 | 0.276 | 0.174 |
| B. subtilis | 0.292 | 0.162 | 0.551 | 0.348 |
| S. aureus | 1.168 | 0.323 | 1.10 | 0.696 |
| *Methicillin resistant S. aureus | 2.335 | 0.323 | 2.2 | 2.785 |
| *E. feacalis | 0.584 | 0.162 | 2.205 | 0.696 |
| Vancomycin resistant E. faecium | N.D | 0.155 | N.D | N.D |
| Vancomycin resistant E. feacalis | N.D | 0.155 | N.D | N.D |
| Gram negative bacteria | | | | |
| *E. coli | 0.584 | 0.646 | 1.10 | 1.392 |
| *K. pneumoniae | >18.68 | 10.34 | >17.64 | 5.57 |
| P. aeruginosa PAO1 | 1.168 | 0.323 | 17.64 | 1.392 |
| Y. pestis | 18.68 | 20.68 | 8.82 | 1.392 |
| *Burkholderia mallei | 9.34 | 10.34 | 8.82 | 11.14 |
| *Burkholderia pseudomallei | 18.68 | >20.68 | >17.64 | 2.785 |
| ¶Burkholderia thailandensis | 18.68 | 20.68 | 17.64 | 2.784 |
| *B. cepacia | 18.68 | >20.68 | 4.41 | 22.28 |

*Clinical isolate
¶Environment
N.D—Not Determined

The effects of Compounds on B. anthracis Spore Germination

B. anthracis spores germinate within minutes following contact with a suitable medium, e.g. the moist tissue of the human respiratory system. Spore germination is usually detected in vitro by alterations in the spore refractility, heat resistance, and staining. Upon germination, spores will become non-refractile, increasing phase dark, susceptible to heat induced death, and stainable with dyes such as Wright-Giemsa stain. To determine the effects of the compounds on spore germination, NSC 317881 was selected for further study. Sterne spores were germinated in Muller Hinton medium in the presence of DMSO (control) or NSC 317881 (1 µM). At time intervals of 0, 15, and 30 minutes, samples were heated at 65° C. for 30 minutes and after cooling on ice, appropriate dilutions of the spores were plated on sheep blood agar plates. The next day, colonies were counted. The % survival was determined by comparing the colony count at different time points to that of the sample collected at time $t_0$. FIG. 2 shows the percent survival plotted against time.

Spores treated with NSC 317881 were killed by heat within 15 minutes following their contact with suitable germination medium, thereby suggesting that spore germination is not affected by the compound. A loss in refractility (FIG. 1B1) further confirms the observation that the compound does not have an effect on spore germination. Likewise, NSC 317880, NSC 330687 and NSC 369718 were tested and results to those of NSC 317881 were obtained.

Time Dependent Killing of B. anthracis Spores

Figure 3:
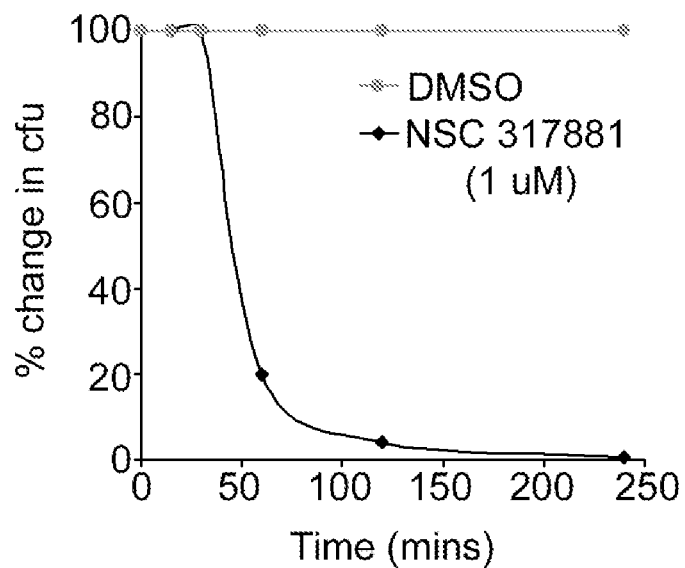

Since the potent compounds had no effect on spore germination, but did inhibit outgrowth, NSC 317881 was examined for time dependent killing of sterne GFP spores. Sterne GFP spores were treated with DMSO (control) or NSC 317881 (1 µM), and at various time intervals appropriate dilutions of the spores were plated on sheep blood agar plates. Ther next day, colonies were counted, and percent reduction in colony forming units (cfu) as compared to the DMSO control was plotted. As shown in FIG. 3, there was a considerable reduction in the cfu after about 60 minutes of treatment with the compound. No viable spores were detected after about a 4 hour treatment with the compound.

Determination of Minimum Bactericidal Concentration (MBC) of the Most Potent Bioactive Compounds To determine if the identified bioactive compounds were bactericidal, several strains of gram positive bacteria were selected, including B. anthracis ciprofloxacin resistant Ames strains and B. anthracis Ames spores, and incubated for about 22 hours with different concentrations ranging from 0 µM to 10 µM of NSC 317881, NSC 317880, NSC 330687 and NSC 369718. Twenty-four hours later, bacteria from MIC wells and four wells above the MIC were plated on sheep blood agar plates. The next day, colony counts were made and MBC values that produced about a 99.9% reduction in viable count were determined using methods known in the art. The MBC values of NSC 317881, NSC 317880, NSC 330687 and NSC 369718 against the gram positive bacteria is provided in Table 3.

TABLE 3

MBCs of 4 compounds against selected gram positive bacteria

| Gram positive bacteria | NSC 317880 (µg/ml) | NSC 317881 (µg/ml) | NSC 330687 (µg/ml) | NSC 369718 (µg/ml) |
|---|---|---|---|---|
| Cipro resistant Ames | 1.168 | 1.292 | 4.41 | 0.348 |
| B. anth1024 | 2.336 | 0.646 | 2.206 | 0.696 |
| B. vollum | 1.168 | 0.162 | 1.103 | 0.348 |
| Ames spores | 0.146 | 0.162 | 0.276 | 0.174 |

Figure 4:
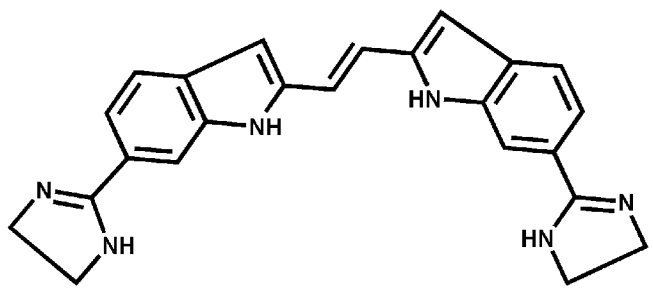
Figure 4:
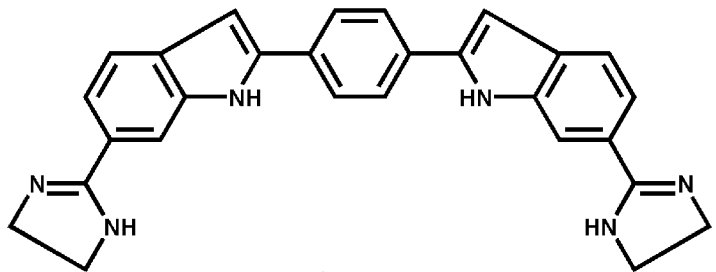
Figure 4:
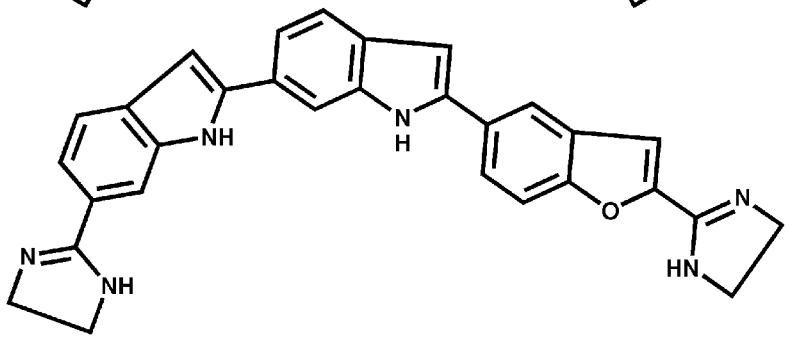
Figure 4:
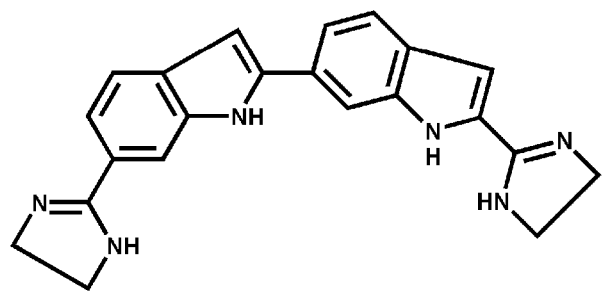

The MBC was defined as the lowest concentration that produced a 99.9% reduction in viable count Structures of the Most Potent Bioactive Compounds The structural formulas of NSC 317880, NSC 317881, NSC 330687 and NSC 369718 are shown in FIG. 4. The structural formulas of the other compounds provided in Table 1 may be obtained from NCBI Pubmed compound database at the world wide web at ncbi.nlm.nih.gov and other compound databases available in the art. Conformational analysis of a representative number of the compounds of the present invention indicate that the compounds favor a planar tertiary conformation, as the compounds are all highly conjugated systems. NSC 317880, NSC 317881 and NSC 330687 are often referred to as diarylimidazolines, as each possesses two indoles, with each of the indoles substituted with an imidazolyl at its six position. NSC 317880, NSC 317881 and NSC 330687 are a congeneric series that canvasses the structure-activity relationship of related structures. As provided in Table 2, the type of linker (see Structural Formula I) can result in structural differences that translate into large MIC variations from one bacterial species to another bacterial species. NSC 369718 is often referred to as a triarylimidazoline which comprises two indoles and one benzofuran. As with the other three compounds, the imidazolyl substitutions occur at the six positions. See FIG. 4. In general, these compounds exhibit common structural features, including a planar tertiary structure and indoles/furan rings that are substituted with two ionizable imidazolyl functional groups (one at either end of the molecules). Therefore, in some embodiments, the present invention is directed to a planar tertiary structure and indoles/furan rings that are substituted with two ionizable imidazolyl functional groups.

Various compounds of the present invention, including NSC 308574, NSC 341909, NSC 240898 and NSC 34190, have been found to inhibit botulinum neurotoxin serotype A light chain metalloprotease activity. Various compounds of the present invention, including NSC 240898, NSC 266474, NSC 266476, NSC 290107, NSC 290108, NSC 290109, NSC 294200, NSC 294201, NSC 294203, NSC 294204, NSC 294206, NSC 300511, NSC 308571, NSC 308572, NSC 308574, NSC 317880, NSC 317881, NSC 317884, NSC 317885, 317886, NSC 317887, NSC 341907, NSC 341909, and NSC 341911 are also found to inhibit the protease activity of anthrax lethal factor. Thus, not only is the present invention directed to methods of inhibiting, reducing or preventing growth of or destroying bacteria of at least one bacterial strain, such as *Clostridium* or *Bacillus*, preferably *Clostridium botulinium* or *Bacillus anthracis*, but it is also directed to methods of inhibiting toxin activity, such as botulinum neurotoxin serotype A light chain metalloprotease activity or the protease activity of anthrax lethal factor. The present invention is also directed to methods of treating a subject suffering from a bacterial infection or intoxication.

Thus, the compounds of the present invention may be used as broad spectrum antibiotics that may provide rapid and effective treatment by eliminating the need to identify the bacterial strain before treatment can be administered. The compounds of the present invention may be used to prevent, inhibit or reduce the growth and spread of bacteria. Further, the compounds of the present invention may be used prophylactically, i.e. administered to a subject prior to exposure or likely exposure to bacteria or bacterial toxins.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A method of inhibiting or reducing growth of bacteria of at least one bacterial strain which comprises contacting the bacteria with an effective amount of at least one compound having the following structural formula:

where Y is or wherein:
n is 1 or 2;
$X^1$ is NH or $NR^8$;
$X^2$ is $CR^7$,
$X^3$ and $X^6$ are each independently N or $CR^7$; $X^4$ and $X^5$ are each independently NH, O, or $NR^8$,
wherein, when Y is L is a linker which is where Z is an optionally substituted phenyl; and
wherein, when Y is L is a linker which is a direct bond or is where Z is an optionally substituted alkyl, alkenyl, dialkenyl, trialkenyl, or aryl;
$R^1$, $R^2$, $R^3$, $R^4$, and $R^6$ are each independently hydrogen, amino, amine with stabilized carbocations, carboxyl, optionally substituted alkyl, alkenyl, alkynyl, cycloalkyl, heterocycloalkyl, aryl, heteroaryl, alkoxy, aryloxy, cycloalkoxy, heteroaryloxy, alkoxycarbonyl, alkylamino, carbamoyl, alkylaminocarbonyl, alkylsulfhydryl, alkylhydroxymate;
$R^7$ is hydrogen or alkyl; and
$R^8$ is OH, a halogen, or an optionally substituted alkyl;
or pharmaceutically acceptable salts thereof.

2. The method of claim 1, wherein at least one of $R^1$, $R^2$, $R^3$, or $R^4$ is hydrogen, amidine, 2-imidazoline, amino, guanidine, methyl, aminomethyl-hydroxamine, or methylamine-guanidine.

3. The method of claim 1, wherein $R^6$ is hydrogen, amidine, benzamidine, benzimidazoline, imidazoline, guanidine, imidazole, oxazole, benzofuran-2-yl-imidazoline, benzofuran-2-yl-amidine, benzofuran-2-yl-guanidine, benzothiophene-2-yl-imidazoline, benzothiophene-2-yl-amidine, benzene-2-yl-amidine, benzofuran-2-yl-imidazole, or benzofuran-2-yl-oxazole.

4. The method of claim 1, wherein at least one of $R^1$, $R^2$, $R^3$, $R^4$, or $R^6$ is —H, —$CH_3$, —$NH_2$,

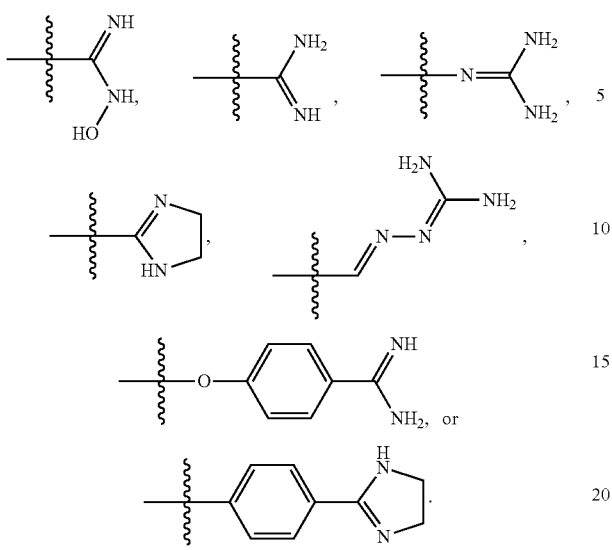

5. The method of claim 1, wherein $R^6$ is

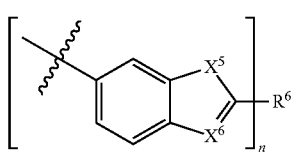

6. The method of claim 1, wherein $R^7$ is —H or —CH$_3$.

7. The method of claim 1, wherein $R^8$ is —(CH$_2$)$_2$OH, or —(CH$_2$)$_2$Cl.

8. The method of claim 1, when Y is

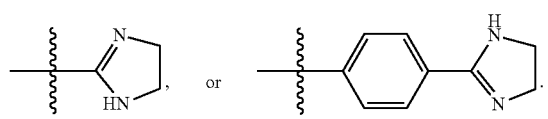 [SMILES: *C1=NCCN1 ; *c1ccc(C2=NCCN2)cc1]

L is a direct bond,

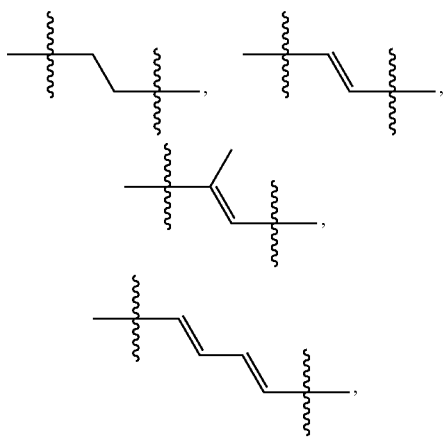

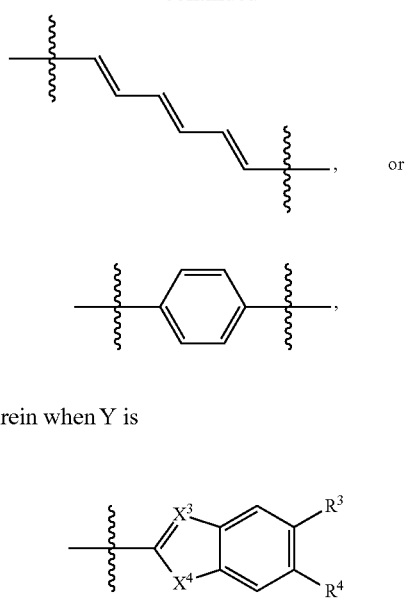

and wherein when Y is

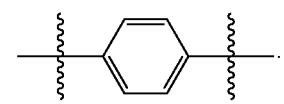

L is

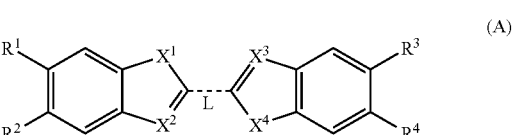

9. The method of claim 1, wherein the compound has the following structural formulae:

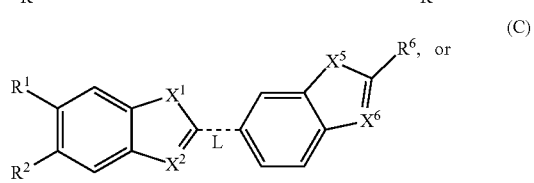

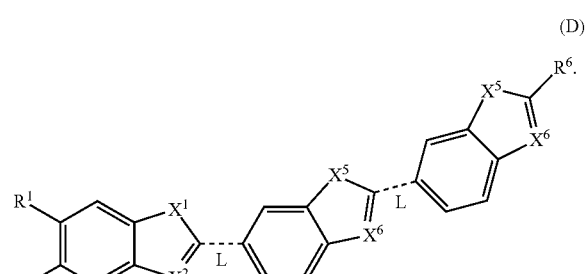

10. A method of inhibiting or reducing growth of bacteria of at least one bacterial strain which comprises contacting the bacteria with an effective amount of at least one compound having the following structural formula:

11. The method of claim 1, wherein the bacterial strain belongs to *Bacillus, Burkholderia, Enterobacter, Escherichia, Helicobacter, Klebsiella, Mycobacterium, Neisseria, Pseudomonas, Staphylococcus, Streptococcus, Yersinia*, or drug resistant strains thereof.

12. The method of claim 1, wherein the bacterial strain is *B. anthracis, B. brevis, B. licheniformis, B. megaterium, B. pumilus, B. subtilis, B. vollum, B. cepacia, B. mallei, M. pseudomallei, B. thailandensis, E. coli, E. feacalis, E. faecium, K. pneumoniae, P. aeruginosa, S. aureous, Y. pestis*, or drug resistant strains thereof.

13. The method of claim 1, wherein the bacteria are two or more bacterial strains.

14. The method of claim 1, wherein the compound is in the form of a pharmaceutical composition.

15. A method of inhibiting or reducing growth of bacteria of more than one bacterial strain which comprises contacting the bacteria with an effective amount of at least one compound having the following structural formula:

wherein:
n is 1 or 2;
$X^1$ is NH or $NR^8$;
$X^2$ is $CR^7$,
$X^3$ and $X^6$ are each independently N or $CR^7$; $X^4$ and $X^5$ are each independently NH, O, or $NR^8$,
wherein, when Y is L is a linker which is where Z is an optionally substituted phenyl; and
wherein, when Y is L is a linker which is a direct bond or is where Z is an optionally substituted alkyl, alkenyl, dialkenyl, trialkenyl, or aryl;
$R^1$, $R^2$, $R^3$, $R^4$, and $R^6$ are each independently hydrogen, amino, amine with stabilized carbocations, carboxyl, optionally substituted alkyl, alkenyl, alkynyl, cycloalkyl, heterocycloalkyl, aryl, heteroaryl, alkoxy, aryloxy, cycloalkoxy, heteroaryloxy, alkoxycarbonyl, alkylamino, carbamoyl, alkylaminocarbonyl, alkylsulfhydryl, alkylhydroxymate;
$R^7$ is hydrogen or alkyl; and
$R^8$ is OH, a halogen, or an optionally substituted alkyl;
or pharmaceutically acceptable salts thereof.

16. The method of claim 1, wherein $X^2$ is CH.

17. The method according to claim 1, wherein said effective amount of said compound is also effective to kill said bacteria.

18. The method according to claim 15, wherein said effective amount of said compound is also effective to kill said bacteria.

* * * * *